United States Patent
Bigner et al.

(10) Patent No.: US 9,441,048 B2
(45) Date of Patent: Sep. 13, 2016

(54) ANTIBODY FOR 3'-ISOLM1 AND 3',6'-ISO-LD1 GANGLIOSIDES

(75) Inventors: Darell Bigner, Mebane, NC (US); Chien-Tsun Kuan, Cary, NC (US); Ira H. Pastan, Potomac, MD (US); Hailan Piao, Durham, NC (US)

(73) Assignees: The United States of America as represented by the Secretary of Health and Human Services, Washington, DC (US); Duke University, Durham, NC (US)

( * ) Notice: Subject to any disclaimer, the term of this patent is extended or adjusted under 35 U.S.C. 154(b) by 339 days.

(21) Appl. No.: 13/988,696

(22) PCT Filed: Nov. 15, 2011

(86) PCT No.: PCT/US2011/060759
§ 371 (c)(1),
(2), (4) Date: Sep. 27, 2013

(87) PCT Pub. No.: WO2012/071216
PCT Pub. Date: May 31, 2012

(65) Prior Publication Data
US 2014/0010829 A1 Jan. 9, 2014

Related U.S. Application Data

(60) Provisional application No. 61/419,317, filed on Dec. 3, 2010, provisional application No. 61/416,096, filed on Nov. 22, 2010.

(51) Int. Cl.
*C07K 16/30* (2006.01)
*A61K 51/10* (2006.01)
*A61K 47/48* (2006.01)
*C07K 16/44* (2006.01)
*A61K 39/00* (2006.01)

(52) U.S. Cl.
CPC ......... *C07K 16/30* (2013.01); *A61K 47/48369* (2013.01); *A61K 47/48415* (2013.01); *A61K 47/48484* (2013.01); *A61K 47/48623* (2013.01); *C07K 16/3084* (2013.01); *C07K 16/44* (2013.01); *A61K 2039/505* (2013.01); *A61K 2039/507* (2013.01); *C07K 2317/622* (2013.01); *C07K 2317/73* (2013.01); *C07K 2317/77* (2013.01); *C07K 2317/92* (2013.01); *C07K 2319/55* (2013.01)

(58) Field of Classification Search
None
See application file for complete search history.

(56) References Cited

U.S. PATENT DOCUMENTS

| | | | |
|---|---|---|---|
| 5,750,078 A * | 5/1998 | Shitara | C07K 16/18 424/130.1 |
| 7,425,622 B2 | 9/2008 | Rosen | |
| 2003/0103963 A1* | 6/2003 | Cheung | 424/130.1 |
| 2004/0133357 A1 | 7/2004 | Zhong et al. | |
| 2005/0215770 A1 | 9/2005 | Bell et al. | |
| 2011/0003336 A1* | 1/2011 | Vidarsson | C07K 16/00 435/69.6 |

FOREIGN PATENT DOCUMENTS

WO 94/03629 A1 2/1994

OTHER PUBLICATIONS

Paul, Fundamental Immunology, 3rd Edition, 1993, pp. 292-295.*
Rudikoff et al. (Proceedings of the National Academy of Sciences USA, vol., 79, p. 1979, 1982).*
Fredman (Biochimica et Biophysica Acta, vol. 1045, p. 239-244, 1990).*
Wikstrand (Progress in Brain Research, vol. 101, p. 213-223, 1994).*
Caron (Journal of Experimental Medicine, vol. 176, p. 1191-1195, 1992).*
Stevenson (Anti-Cancer Drug Design, vol. 3, p. 219-230, 1989).*
Kato, Y., et al., "GMab-1, a high-affinity anti-3'-isoLM1/3',6'-isoLD1 IgG monoclonal antibody, raised in lacto-series ganglioside-defective knockout mice," Biochemical and Biophysical Research Communications, 2010, pp. 750-755, vol. 391, Elsevier, USA.
International Search Report issued May 21, 2012, in PCT/US11/60759.

* cited by examiner

*Primary Examiner* — Michael D Allen
(74) *Attorney, Agent, or Firm* — Banner & Witcoff, LTD

(57) ABSTRACT

High affinity antibodies were made to gangliosides expressed on tumor cells. The antibodies can be used analytically, diagnostically, therapeutically, and theranostically. The antibodies may be used to target cytotoxic reagents to tumor cells, thus minimizing full-body toxicity. The antibodies may also be used with out added cytotoxin. The antibodies may be detectably labeled or labelable for analytic and diagnostic purposes. The combination of specificity and affinity of the antibodies render them particularly useful.

5 Claims, 11 Drawing Sheets

|  | VLCDR1 | VHCDR2 |
|---|---|---|
| DMab14-scFv | aat cct agc aac ggt cgt act aac tat aat gag aag ttc aag agc<br>N  P  S  N  G  R  T  N  Y  N  E  K  F  K  S | agc gcc agt gaa agt gtt gag agt tat ggc aat aat ttt atg cac<br>R  A  S  E  S  V  E  S  Y  G  N  N  F  M  H |
| DMab14-86184 | aat cca atg gac tcc cgt act aac tat aat aag aag ttc aag agc<br>N  P  M  D  S  R  T  N  Y  N  K  K  F  K  S | ttg tac ggg gaa agt gtt gag agt tat ggc aat aat ttt atg cac<br>L  Y  G  E  S  V  E  S  Y  G  N  N  F  M  H |

FIG. 5

```
1/1
cat atg cag gtc caa ctg gtg cag cag cct ggg gct gaa ctg gtg aag cct ggg gct tca gtg aag ctg tcc tgc aag gct tct ggc tac acc ttc acc agg tac atg cac tgg gtg aga
 H   M   Q   V   Q   L   Q   Q   P   G   A   E   L   V   K   P   G   A   S   V   K   L   S   C   K   A   S   G   Y   T   F   T   R   Y   M   H   W   V   R
                                  31/11                                                           61/21                                                           91/31

121/41                                                          151/51                                                           181/61                                                          211/71
cag agg cct gga caa ggt ctt gag tgg att gga gag att aat cca atg tcc cgt act aac tat aag aac tat aat aag aag ttc aag agc aag gcc aca ctg act gta gac aaa tcc agc aca
 Q   R   P   G   Q   G   L   E   W   I   G   E   I   N   P   M   S   R   T   N   Y   N   K   K   F   K   S   K   A   T   L   T   V   D   K   S   S   T 241/81                                                          271/91                                                           301/101                                                         331/111
gcc tac atg caa ctc agc agc ctg aaa tct gag gac tct gcg gtc tat tac tgt gca aga cca ggt cgg gct agg atg gac tac tgg ggt caa gga aac tca ggt cac ctc tcc tca
 A   Y   M   Q   L   S   S   L   K   S   E   D   S   A   V   Y   Y   C   A   R   P   G   R   A   R   M   D   Y   W   G   Q   G   N   S   V   T   V   S   S 361/121                                                         391/131                                                          421/141                                                         451/151
ggc gga ggg gga tct ggt ggt ggt gga tct ggc ggt ggc ggc agc ggt ggc gga ggc agt ggt ggc ggt ggc tct ctg cag agg gcc atc ata tcc tgc ttg
 G   G   G   G   S   G   G   G   G   S   G   G   G   G   S   G   N   I   V   L   T   Q   S   P   A   S   L   A   V   S   L   G   Q   R   A   I   I   S   C   L 481/161                                                         511/171                                                          541/181                                                         571/191
tac ggg gaa agt gtt gag agt tat ggc aat aat ttt atg cac tgg tac cag cag aaa cca gga cag cca ccc aaa ctc ctc atc tat ctt gca tcc aac cta gaa tct ggg gtc cct gcc
 Y   G   E   S   V   E   S   Y   G   N   N   F   M   H   W   Y   Q   Q   K   P   G   Q   P   P   K   L   L   I   Y   L   A   S   N   L   E   S   G   V   P   A 601/201                                                         631/211                                                          661/221                                                         691/231
agg ttc agt ggc agt ggg tct agg aca gac ttc acc ctc acc att gat cct gtg gag gct gat gat gca acc tat tac tgt cag caa aat aat gag gat ccc acg ttc gga ggg ggg
 R   F   S   G   S   G   S   R   T   D   F   T   L   T   I   D   P   V   E   A   D   D   A   A   T   Y   Y   C   Q   Q   N   N   E   D   P   T   F   G   G   G 721/241
acc aag ctg gaa ata aaa aaa gct t
 T   K   L   E   I   K   K   A
```

FIG. 6

SEQUENCE LISTING

```
<160> NUMBER OF SEQ ID NOS: 71

<210> SEQ ID NO 1
<211> LENGTH: 15
<212> TYPE: PRT
<213> ORGANISM: Artificical Sequence
<220> FEATURE:
<223> OTHER INFORMATION: hybrid human and mouse

<400> SEQUENCE: 1

Asn Pro Met Asp Ser Arg Thr Asn Tyr Asn Lys Lys Phe Lys Ser
1               5                   10                  15

<210> SEQ ID NO 2
<211> LENGTH: 15
<212> TYPE: PRT
<213> ORGANISM: Artificical Sequence
<220> FEATURE:
<223> OTHER INFORMATION: hybrid human and mouse

<400> SEQUENCE: 2

Leu Tyr Gly Glu Ser Val Glu Ser Tyr Gly Asn Asn Phe Met His
1               5                   10                  15

<210> SEQ ID NO 3
<211> LENGTH: 45
```

-continued

```
<212> TYPE: DNA
<213> ORGANISM: Articifical Sequence
<220> FEATURE:
<223> OTHER INFORMATION: hybrid human and mouse

<400> SEQUENCE: 3
aatccaatgg actcccgtac taactataat aagaagttca agagc            45

<210> SEQ ID NO 4
<211> LENGTH: 45
<212> TYPE: DNA
<213> ORGANISM: Articifical Sequence
<220> FEATURE:
<223> OTHER INFORMATION: hybrid human and mouse

<400> SEQUENCE: 4
ttgtacgggg aaagtgttga gagttatggc aataatttta tgcac            45

<210> SEQ ID NO 5
<211> LENGTH: 745
<212> TYPE: DNA
<213> ORGANISM: Articifical Sequence
<220> FEATURE:
<223> OTHER INFORMATION: hybrid human and mouse; DMab14-86184

<400> SEQUENCE: 5
catatgcagg tccaactgca gcagcctggg gctgaactgg tgaagcctgg ggcttcagtg     60
aagctgtcct gcaaggcttc tggctacacc ttcaccaggt actggatgca ctgggtgaga    120
cagaggcctg gacaaggtct tgagtggatt ggagagatta atccaatgga ctcccgtact    180
aactataata agaagttcaa gagcaaggcc acactgactg tagacaaatc ctccagcaca    240
gcctacatgc aactcagcag cctgaaatct gaggactctg cggtctatta ctgtgcaaga    300
ccaggtcggg ctaggggtat ggactactgg ggtcaaggaa actcagtcac cgtctcctca    360
ggcggagggg gatctggtgg tggcggatct ggaggtggcg gcagcggtaa cattgtgctg    420
acccaatctc cagcttcttt ggctgtgtct ctagggcaga gggccatcat atcctgcttg    480
tacggggaaa gtgttgagag ttatggcaat aattttatgc actggtacca gcagaaacca    540
ggacaggcac ccaaactcct catctatctt gcatccaacc tagaatctgg ggtccctgcc    600
aggttcagtg gcagtgggtc taggacagac ttcaccctca ccattgatcc tgtggaggct    660
gatgatgctg caacctatta ctgtcagcaa aataatgagg atcccacgtt cggagggggg    720
accaagctgg aaataaaaaa agctt                                         745

<210> SEQ ID NO 6
<211> LENGTH: 248
<212> TYPE: PRT
<213> ORGANISM: Articifical Sequence
<220> FEATURE:
<223> OTHER INFORMATION: hybrid human and mouse; DMab14-86184

<400> SEQUENCE: 6

His Met Gln Val Gln Leu Gln Gln Pro Gly Ala Glu Leu Val Lys Pro
  1               5                  10                  15

Gly Ala Ser Val Lys Leu Ser Cys Lys Ala Ser Gly Tyr Thr Phe Thr
                 20                  25                  30

Arg Tyr Trp Met His Trp Val Arg Gln Arg Pro Gly Gln Gly Leu Glu
             35                  40                  45

Trp Ile Gly Glu Ile Asn Pro Met Asp Ser Arg Thr Asn Tyr Asn Lys
         50                  55                  60
```

```
Lys Phe Lys Ser Lys Ala Thr Leu Thr Val Asp Lys Ser Ser Thr
 65                  70                  75                  80

Ala Tyr Met Gln Leu Ser Ser Leu Lys Ser Glu Asp Ser Ala Val Tyr
             85                  90                  95

Tyr Cys Ala Arg Pro Gly Arg Ala Arg Gly Met Asp Tyr Trp Gly Gln
            100                 105                 110

Gly Asn Ser Val Thr Val Ser Ser Gly Gly Gly Ser Gly Gly
        115                 120                 125

Gly Ser Gly Gly Gly Ser Gly Asn Ile Val Leu Thr Gln Ser Pro
    130                 135                 140

Ala Ser Leu Ala Val Ser Leu Gly Gln Arg Ala Ile Ile Ser Cys Leu
145             150                 155                 160

Tyr Gly Glu Ser Val Glu Ser Tyr Gly Asn Asn Phe Met His Trp Tyr
                165                 170                 175

Gln Gln Lys Pro Gly Gln Ala Pro Lys Leu Leu Ile Tyr Leu Ala Ser
            180                 185                 190

Asn Leu Glu Ser Gly Val Pro Ala Arg Phe Ser Gly Ser Gly Ser Arg
        195                 200                 205

Thr Asp Phe Thr Leu Thr Ile Asp Pro Val Glu Ala Asp Asp Ala Ala
    210                 215                 220

Thr Tyr Tyr Cys Gln Gln Asn Asn Glu Asp Pro Thr Phe Gly Gly
225             230                 235                 240

Thr Lys Leu Glu Ile Lys Lys Ala
                245
```

<210> SEQ ID NO 7
<211> LENGTH: 15
<212> TYPE: PRT
<213> ORGANISM: Artificical Sequence
<220> FEATURE:
<223> OTHER INFORMATION: hybrid human and mouse

<400> SEQUENCE: 7

```
Asn Pro Ser Asn Gly Arg Thr Asn Tyr Asn Glu Lys Phe Lys Ser
 1               5                  10                  15
```

<210> SEQ ID NO 8
<211> LENGTH: 15
<212> TYPE: PRT
<213> ORGANISM: Artificical Sequence
<220> FEATURE:
<223> OTHER INFORMATION: hybrid human and mouse

<400> SEQUENCE: 8

```
Arg Ala Ser Glu Ser Val Glu Ser Tyr Gly Asn Asn Phe Met His
 1               5                  10                  15
```

<210> SEQ ID NO 9
<211> LENGTH: 45
<212> TYPE: DNA
<213> ORGANISM: Artificical Sequence
<220> FEATURE:
<223> OTHER INFORMATION: hybrid human and mouse

<400> SEQUENCE: 9
aatcctagca acggtcgtac taactataat gagaagttca agagc                45

<210> SEQ ID NO 10
<211> LENGTH: 45
<212> TYPE: DNA
<213> ORGANISM: Artificical Sequence

```
<220> FEATURE:
<223> OTHER INFORMATION: hybrid human and mouse

<400> SEQUENCE: 10
agagccagtg aaagtgttga gagttatggc aataatttta tgcac                45

<210> SEQ ID NO 11
<211> LENGTH: 115
<212> TYPE: PRT
<213> ORGANISM: Artificical Sequence
<220> FEATURE:
<223> OTHER INFORMATION: ScFv antibodies or portion thereof; GMab1-VH

<400> SEQUENCE: 11

Glu Val Gln Leu Gln Gln Ser Gly Pro Glu Leu Val Lys Pro Gly Ala
 1               5                   10                  15

Ser Val Lys Ile Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Asp Ile Asn Pro Asn Asn Gly Gly Thr Ser Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Thr Tyr Gly Leu Gly Gly Tyr Trp Gly Gln Gly Thr Thr Leu Thr
            100                 105                 110

Val Ser Ser
        115

<210> SEQ ID NO 12
<211> LENGTH: 108
<212> TYPE: PRT
<213> ORGANISM: Artificical Sequence
<220> FEATURE:
<223> OTHER INFORMATION: ScFv antibodies or portion thereof; GMab1-VL

<400> SEQUENCE: 12

Gly Asn Ile Val Met Thr Gln Ser Pro Lys Ser Met Ser Met Ser Val
 1               5                   10                  15

Gly Glu Arg Val Thr Gln Thr Cys Lys Ala Ser Glu Asn Val Val Thr
            20                  25                  30

Tyr Val Ser Trp Tyr Gln Leu Lys Pro Glu Gln Ser Pro Lys Leu Leu
        35                  40                  45

Ile Tyr Gly Ala Ser Asn Arg Tyr Thr Gly Val Pro Asp Arg Phe Thr
    50                  55                  60

Gly Ser Gly Ser Ala Thr Asp Phe Thr Leu Thr Ile Ser Ser Val Gln
65                  70                  75                  80

Ala Glu Asp Leu Ala Asp Tyr His Cys Gly Gln Gly Tyr Ser Tyr Pro
                85                  90                  95

Tyr Thr Phe Gly Gly Gly Thr Lys Leu Glu Ile Lys
            100                 105

<210> SEQ ID NO 13
<211> LENGTH: 115
<212> TYPE: PRT
<213> ORGANISM: Artificical Sequence
<220> FEATURE:
<223> OTHER INFORMATION: ScFv antibodies or portion thereof; GMab2-VH
```

<400> SEQUENCE: 13

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Thr Ile Ser Asp Gly Gly Tyr Tyr Thr Tyr Tyr Pro Asp Asn Val
    50                  55                  60

Lys Gly Arg Phe Thr Ile Ser Arg Asp Asn Ala Lys Asn Asn Leu Tyr
65                  70                  75                  80

Leu Gln Met Ser His Leu Lys Ser Gly Asp Thr Ala Met Tyr Tyr Cys
                85                  90                  95

Ala Arg Tyr Asp Ser Phe Asp Tyr Trp Gly Gln Gly Thr Thr Leu Thr
            100                 105                 110

Val Ser Ser
        115

<210> SEQ ID NO 14
<211> LENGTH: 111
<212> TYPE: PRT
<213> ORGANISM: Artificical Sequence
<220> FEATURE:
<223> OTHER INFORMATION: ScFv antibodies or portion thereof; GMab2-VL

<400> SEQUENCE: 14

Gly Asp Ile Val Leu Thr Gln Ser Pro Ala Ser Leu Ala Val Ser Leu
1               5                   10                  15

Gly Gln Arg Ala Thr Ile Ser Tyr Arg Ala Ser Lys Ser Val Ser Thr
            20                  25                  30

Ser Gly Tyr Ser Tyr Met His Trp Asn Gln Gln Lys Pro Gly Gln Pro
        35                  40                  45

Pro Arg Leu Leu Ile Tyr Leu Val Ser Asn Leu Glu Ser Gly Val Pro
    50                  55                  60

Ala Arg Phe Ser Gly Ser Gly Ser Gly Thr Asp Phe Thr Leu Asn Ile
65                  70                  75                  80

His Pro Val Glu Glu Glu Asp Ala Ala Thr Tyr Tyr Cys Gln His Ile
                85                  90                  95

Arg Glu Leu Thr Thr Phe Gly Gly Gly Thr Lys Leu Glu Ile Lys
            100                 105                 110

<210> SEQ ID NO 15
<211> LENGTH: 727
<212> TYPE: DNA
<213> ORGANISM: Artificial Sequence
<220> FEATURE:
<223> OTHER INFORMATION: ScFv antibodies or portion thereof; DMab1-scFv

<400> SEQUENCE: 15
catatggagg tccagctgca acaatctgga cctgagctgg tgaagcctgg ggcttcagtg    60
aagatatcct gtaaggcttc tggatacacg ttcactgact actacatgaa ctgggtgaag   120
cagagccatg gaaagagcct tgagtggatt ggagatatta atcctaacaa tggtggtact   180
agctacaacc agaagttcaa gggcaaggcc acattgactg tagacaagtc ctccagcacc   240
gcctacatga gctccgcag cctgacctct gaggactctg cagtctatta ctgtgcaact   300
tatggactgg gaggctactg gggccaaggc accactctca cagtctcctc aggcggaggg   360

```
ggatccggtg gtggcggatc tggaggtggc ggcagcggga acattgtaat gacccaatct    420
cccaaatcca tgtccatgtc agtaggagag agggtcacct tgacctgcaa ggccagtgag    480
aatgtggtta cttatgtttc ctggtatcaa ctgaaaccag agcagtctcc taaactgctg    540
atatacgggg catccaaccg gtacactggg gtccccgatc gcttcacagg cagtggatct    600
gcaacagatt tcactctgac catcagcagt gtgcaggctg aagaccttgc agattatcac    660
tgtggacagg gttacagcta tccgtacacg ttcggagggg ggaccaagct ggaaataaaa    720
aaagctt                                                              727
```

<210> SEQ ID NO 16
<211> LENGTH: 723
<212> TYPE: DNA
<213> ORGANISM: Articifical Sequence
<220> FEATURE:
<223> OTHER INFORMATION: ScFv antibodies or portion thereof; DMab2-scFv

<400> SEQUENCE: 16

```
gaagtgcagc tggtggagtc tgggggaggc ttagtgaagc ctggagggtc cctgaaactc    60
tcctgtgcag cctctggatt cactttcagt agctatgcca tgtcttgggt tcgccagact    120
ccggaaaaga ggctggagtg ggtcgcaacc attagtgatg gtggttatta cacgtactat    180
ccagacaatg taagggccg attcaccatc tccagagaca tgccaagaa caacctgtac    240 ctgcaaatga gccatctgaa gtctggggac acagccatgt attactgtgc aagatatgac    300
tcctttgact actggggcca aggcaccact ctcacagtct cctcaggcgg agggggatcc    360
ggtggtggcg gatctggagg tggcggcagc ggtgacattg tgctgacaca gtctcctgct    420
tccttagctg tatctctggg gcagagggcc accatctcat acagggccag caaaagtgtc    480
agtacatctg gctatagtta tatgcactgg aaccaacaga aaccaggaca gccacccaga    540
ctcctcatct atcttgtatc caacctagaa tctggggtcc ctgccaggtt cagtggcagt    600
gggtctggga cagacttcac cctcaacatc catcctgtgg aggaggagga tgctgcaacc    660
tattactgtc agcacattag ggagcttaca cgttcggag ggggaccaa gctggaaata    720 aaa                                                                   723
```

<210> SEQ ID NO 17
<211> LENGTH: 722
<212> TYPE: DNA
<213> ORGANISM: Articifical Sequence
<220> FEATURE:
<223> OTHER INFORMATION: scFv; GMab1

<400> SEQUENCE: 17

```
atggaggtcc agctgcaaca atctggacct gagctggtga agcctggggc ttcagtgaag    60
atatcctgta aggcttctgg atacacgttc actgactact acatgaactg ggtgaagcag    120
agccatggaa agagccttga gtggattgga gatattaatc ctaacaatgg tggtactagc    180
tacaaccaga agttcaaggg caaggccaca ttgactgtag acaagtcctc cagcaccgcc    240
tacatggagc tccgcagcct gacctctgag gactctgcag tctattactg tgcaacttat    300
ggcctgggag gctactgggg ccaaggcacc actctcacag tctcctcagg cggagggga    360 tctggtggtg gcggatctgg aggtggcggc agcgggaata ttgtaatgac ccaatctccc    420
aaatccatgt ccatgtcagt aggagagagg gtcaccttga cctgcaaggc cagtgagaat    480
gtggttactt atgtttcctg gtatcaacag aaaccagagc agtctcctaa actgctgata    540
```

```
tacggggcat ccaaccggta cactggggtc cccgatcgct tcacaggcag tggttctgca      600
acagatttca ctctgaccat cagcagtgtg caggctgaag accttgcaga ttatcactgt      660
ggacagggtt acagctatcc gtacacgttc ggaggggga ccaagctgga agtaaaaaaa       720
gt                                                                    722
```

<210> SEQ ID NO 18
<211> LENGTH: 736
<212> TYPE: DNA
<213> ORGANISM: Artificial Sequence
<220> FEATURE:
<223> OTHER INFORMATION: scFv; GMab2

<400> SEQUENCE: 18

```
catatggaag tgcagctggt ggagtctggg ggaggcttag tgaagcctgg agggtccctg       60
aaactctcct gtgcagcctc tggattcact ttcagtagct atgccatgtc ttgggctcgc      120
cagactccgg aaaagaggct ggagtgggtc gcaaccatta gtgatggtgg ttattacacg      180
tactatccag acaatgtaaa gggccgattc accatctcca gagacaatgc caagaacaac      240
ctgtacctgc aaatgagcca tctgaagtct ggggacacag ccatgtatta ctgtgcaaga      300
tatgactcct ttgactactg gggccaaggc accactctca cagtctcctc aggcggaggg      360
ggatccggtg gtggcggatc tagaggtggc ggcagcggtg acattgtgct gacacagtct      420
cctgcttcct tagctgtatc tctggggcag agggccacca tctcatacag ggccagcaaa      480
agtgtcagta catctggcta tagttatatg cactggaacc aacagaaacc aggacagcca      540
cccagactcc tcatctatct tgtatccaac ctagaatctg gggtccctgc caggttcagt      600
ggcagtgggt ctgggacaga cttcaccctc aacatccatc ctgtggagga ggaggatgct      660
gcaacctatt actgtcagca cattagggag cttacaacgt tcggaggggg gaccaagctg      720
gaaataaaaa aagctt                                                     736
```

<210> SEQ ID NO 19
<211> LENGTH: 732
<212> TYPE: DNA
<213> ORGANISM: Artificial Sequence
<220> FEATURE:
<223> OTHER INFORMATION: DMab14 scFV

<400> SEQUENCE: 19

```
caggtccaac tgcagcagcc tggggctgaa ctggtgaagc ctggggcttc agtgaagctg       60
tcctgcaagg cttctggcta caccttcacc aggtactgga tgcactgggt gagacagagg      120
cctggacaag gtcttgagtg gattggagag attaatccta gcaacggtcg tactaactat      180
aatgagaagt tcaagagcaa ggccacactg actgtagaca atcctccag cacagcctac       240 atgcaactca gcagcctgaa atctgaggac tctgcggtct attactgtgc aagaccaggt      300
cgggctaggg gtatggacta ctggggtcaa ggaaactcag tcaccgtctc ctcaggcgga      360
gggggatccg gtggtggcgg atctgaggt ggcggcagcg taacattgt gctgacccca       420 tctccagctt ctttggctgt gtctctaggg cagagggcca ccatatcctg cagagccagt      480
gaaagtgttg agagttatgg caataatttt atgcactggt accagcagaa accaggacag      540
gcacccaaac tcctcatcta tcttgcatcc aacctagaat ctggggtccc tgccaggttc      600
agtggcagtg gtctaggac agacttcacc ctcaccatcg atcccgtgga ggctgatgat      660
gctgcaacct attactgtca gcaaaataat gaggatccca cgttcggagg ggggaccaag      720
ctggaaataa aa                                                         732
```

-continued

<210> SEQ ID NO 20
<211> LENGTH: 225
<212> TYPE: PRT
<213> ORGANISM: Artificical Sequence
<220> FEATURE:
<223> OTHER INFORMATION: scFv GMab1

<400> SEQUENCE: 20

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Asp Ile Asn Pro Asn Asn Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Thr Tyr Gly Leu Gly Gly Tyr Trp Gly Gln Gly Thr Thr Leu Thr
            100                 105                 110

Val Ser Ser Gly Asn Ile Val Met Thr Gln Ser Pro Lys Ser Met Ser
        115                 120                 125

Met Ser Val Gly Glu Arg Val Thr Leu Thr Cys Lys Ala Ser Glu Asn
    130                 135                 140

Val Val Thr Tyr Val Ser Trp Tyr Gln Gln Lys Pro Glu Gln Ser Pro
145                 150                 155                 160

Lys Leu Leu Ile Tyr Gly Ala Ser Asn Arg Tyr Thr Gly Val Pro Asp
                165                 170                 175

Arg Phe Thr Gly Ser Gly Ser Ala Thr Asp Phe Thr Leu Thr Ile Ser
            180                 185                 190

Ser Val Gln Ala Glu Asp Leu Ala Asp Tyr His Cys Gly Gln Gly Tyr
        195                 200                 205

Ser Tyr Pro Tyr Thr Phe Gly Gly Gly Thr Lys Leu Glu Val Lys Lys
    210                 215                 220

Ala
225

<210> SEQ ID NO 21
<211> LENGTH: 244
<212> TYPE: PRT
<213> ORGANISM: Artificical Sequence
<220> FEATURE:
<223> OTHER INFORMATION: scFv; GMab2

<400> SEQUENCE: 21

Met Glu Val Gln Leu Val Glu Ser Gly Gly Gly Leu Val Lys Pro Gly
1               5                   10                  15

Gly Ser Leu Lys Leu Ser Cys Ala Ala Ser Gly Phe Thr Phe Ser Ser
            20                  25                  30

Tyr Ala Met Ser Trp Ala Arg Gln Thr Pro Glu Lys Arg Leu Glu Trp
        35                  40                  45

Val Ala Thr Ile Ser Asp Gly Gly Tyr Tyr Thr Tyr Tyr Pro Asp Asn
    50                  55                  60

Val Lys Gly Arg Phe Thr Ile Ser Arg Asp Asn Ala Lys Asn Asn Leu

```
                65                  70                  75                  80
Tyr Leu Gln Met Ser His Leu Lys Ser Gly Asp Thr Ala Met Tyr Tyr
                    85                  90                  95

Cys Ala Arg Tyr Asp Ser Phe Asp Tyr Trp Gly Gln Gly Thr Thr Leu
                    100                 105                 110

Thr Val Ser Ser Gly Gly Gly Gly Ser Gly Gly Gly Gly Ser Arg Gly
                    115                 120                 125

Gly Gly Ser Gly Asp Ile Val Leu Thr Gln Ser Pro Ala Ser Leu Ala
            130                 135                 140

Val Ser Leu Gly Gln Arg Ala Thr Ile Ser Tyr Arg Ala Ser Lys Ser
145                 150                 155                 160

Val Ser Thr Ser Gly Tyr Ser Tyr Met His Trp Asn Gln Gln Lys Pro
                    165                 170                 175

Gly Gln Pro Pro Arg Leu Leu Ile Tyr Leu Val Ser Asn Leu Glu Ser
                    180                 185                 190

Gly Val Pro Ala Arg Phe Ser Gly Ser Gly Ser Gly Thr Asp Phe Thr
                    195                 200                 205

Leu Asn Ile His Pro Val Glu Glu Asp Ala Ala Thr Tyr Tyr Cys
            210                 215                 220

Gln His Ile Arg Glu Leu Thr Thr Phe Gly Gly Gly Thr Lys Leu Glu
225                 230                 235                 240

Ile Lys Lys Ala

<210> SEQ ID NO 22
<211> LENGTH: 230
<212> TYPE: PRT
<213> ORGANISM: Artificical Sequence
<220> FEATURE:
<223> OTHER INFORMATION: scFv; DMab14

<400> SEQUENCE: 22

Met Gln Val Gln Leu Gln Gln Pro Gly Ala Glu Leu Val Lys Pro Gly
1               5                   10                  15

Ala Ser Val Lys Leu Ser Cys Lys Ala Ser Gly Tyr Thr Phe Thr Arg
                20                  25                  30

Tyr Trp Met His Trp Val Arg Gln Arg Pro Gly Gln Gly Leu Glu Trp
            35                  40                  45

Ile Gly Glu Ile Asn Pro Ser Asn Gly Arg Thr Asn Tyr Asn Glu Lys
        50                  55                  60

Phe Lys Ser Lys Ala Thr Leu Thr Val Asp Lys Ser Ser Ser Thr Ala
65                  70                  75                  80

Tyr Met Gln Leu Ser Ser Leu Lys Ser Glu Asp Ser Ala Val Tyr Tyr
                    85                  90                  95

Cys Ala Arg Pro Gly Arg Ala Arg Gly Met Asp Tyr Trp Gly Gln Gly
                100                 105                 110

Asn Ser Val Thr Val Ser Ser Gly Asn Ile Val Leu Thr Gln Ser Pro
            115                 120                 125

Ala Ser Leu Ala Val Ser Leu Gly Gln Arg Ala Thr Ile Ser Cys Arg
        130                 135                 140

Ala Ser Glu Ser Val Glu Ser Tyr Gly Asn Asn Phe Met His Trp Tyr
145                 150                 155                 160

Gln Gln Lys Pro Gly Gln Ala Pro Lys Leu Leu Ile Tyr Leu Ala Ser
                    165                 170                 175

Asn Leu Glu Ser Gly Val Pro Ala Arg Phe Ser Gly Ser Gly Ser Arg
                    180                 185                 190
```

Thr Asp Phe Thr Leu Thr Ile Asp Pro Val Glu Ala Asp Ala Ala
    195                 200                 205

Thr Tyr Tyr Cys Gln Gln Asn Asn Glu Asp Pro Thr Phe Gly Gly Gly
    210                 215                 220

Thr Lys Leu Glu Ile Lys
225             230

<210> SEQ ID NO 23
<211> LENGTH: 36
<212> TYPE: DNA
<213> ORGANISM: Artificical Sequence
<220> FEATURE:
<223> OTHER INFORMATION: primer

<400> SEQUENCE: 23
ggccagtgga tagtcagatg ggggtgtcgt tttggc                           36

<210> SEQ ID NO 24
<211> LENGTH: 21
<212> TYPE: DNA
<213> ORGANISM: Artificial Sequence
<220> FEATURE:
<223> OTHER INFORMATION: primer

<400> SEQUENCE: 24
ggatacagtt ggtgcagcat c                                           21

<210> SEQ ID NO 25
<211> LENGTH: 27
<212> TYPE: DNA
<213> ORGANISM: Artificial Sequence
<220> FEATURE:
<223> OTHER INFORMATION: primer

<400> SEQUENCE: 25
gccgccacca tggaggtcca actgcag                                     27

<210> SEQ ID NO 26
<211> LENGTH: 45
<212> TYPE: DNA
<213> ORGANISM: Artificial Sequence
<220> FEATURE:
<223> OTHER INFORMATION: primer

<400> SEQUENCE: 26
agatccgcca ccaccggatc ccctccgcc tgaggagacg gtgac                  45

<210> SEQ ID NO 27
<211> LENGTH: 45
<212> TYPE: DNA
<213> ORGANISM: Artificial Sequence
<220> FEATURE:
<223> OTHER INFORMATION: primer

<400> SEQUENCE: 27
ggtggtggcg gatctggagg tggcggcagc ggtaacattg tgctg                 45

<210> SEQ ID NO 28
<211> LENGTH: 30
<212> TYPE: DNA
<213> ORGANISM: Artificial Sequence
<220> FEATURE:
<223> OTHER INFORMATION: primer

<400> SEQUENCE: 28
gcagccgaat tcatttttat ttccagcttg    30

<210> SEQ ID NO 29
<211> LENGTH: 27
<212> TYPE: DNA
<213> ORGANISM: Artificical Sequence
<220> FEATURE:
<223> OTHER INFORMATION: primer

<400> SEQUENCE: 29
gccgccacca tggaggtcca actgcag    27

<210> SEQ ID NO 30
<211> LENGTH: 31
<212> TYPE: DNA
<213> ORGANISM: Artificical Sequence
<220> FEATURE:
<223> OTHER INFORMATION: primer

<400> SEQUENCE: 30
atgatgtgcg gccgctttta tttccagctt g    31

<210> SEQ ID NO 31
<211> LENGTH: 36
<212> TYPE: DNA
<213> ORGANISM: Artificical Sequence
<220> FEATURE:
<221> NAME/KEY: misc_feature
<222> LOCATION: (1)...(36)
<223> OTHER INFORMATION: n = A,T,C or G
<223> OTHER INFORMATION: primer

<400> SEQUENCE: 31
gttagtacga ccgttsnnsn nsnnaatctc tccaat    36

<210> SEQ ID NO 32
<211> LENGTH: 39
<212> TYPE: DNA
<213> ORGANISM: Artificical Sequence
<220> FEATURE:
<221> NAME/KEY: misc_feature
<222> LOCATION: (1)...(39)
<223> OTHER INFORMATION: n = A,T,C or G
<223> OTHER INFORMATION: primer

<400> SEQUENCE: 32
aatatagtta gtacgsnnsn nsnnaggatt aatctctcc    39

<210> SEQ ID NO 33
<211> LENGTH: 33
<212> TYPE: DNA
<213> ORGANISM: Artificical Sequence
<220> FEATURE:
<221> NAME/KEY: misc_feature
<222> LOCATION: (1)...(33)
<223> OTHER INFORMATION: n = A,T,C or G
<223> OTHER INFORMATION: primer

<400> SEQUENCE: 33
tacagtcagt gtggcsnnsn nsnngaactt ctc    33

<210> SEQ ID NO 34
<211> LENGTH: 27
<212> TYPE: DNA
<213> ORGANISM: Artificical Sequence
<220> FEATURE:
<223> OTHER INFORMATION: primer

<400> SEQUENCE: 34
gccgccacca tggaggtcca actgcag                                          27

<210> SEQ ID NO 35
<211> LENGTH: 31
<212> TYPE: DNA
<213> ORGANISM: Artificical Sequence
<220> FEATURE:
<223> OTHER INFORMATION: primer

<400> SEQUENCE: 35
atgatgtgcg gccgctttta tttccagctt g                                     31

<210> SEQ ID NO 36
<211> LENGTH: 42
<212> TYPE: DNA
<213> ORGANISM: Artificical Sequence
<220> FEATURE:
<221> NAME/KEY: misc_feature
<222> LOCATION: (1)...(42)
<223> OTHER INFORMATION: n = A,T,C or G
<223> OTHER INFORMATION: primer

<400> SEQUENCE: 36
accatatcct gcnnsnnsnn sgaaagtgtt gagagttatg gc                         42

<210> SEQ ID NO 37
<211> LENGTH: 42
<212> TYPE: DNA
<213> ORGANISM: Artificical Sequence
<220> FEATURE:
<221> NAME/KEY: misc_feature
<222> LOCATION: (1)...(42)
<223> OTHER INFORMATION: n = A,T,C or G
<223> OTHER INFORMATION: primer

<400> SEQUENCE: 37
accatatcct gcagannsnn snnsagtgtt gagagttatg gc                         42

<210> SEQ ID NO 38
<211> LENGTH: 42
<212> TYPE: DNA
<213> ORGANISM: Artificical Sequence
<220> FEATURE:
<221> NAME/KEY: misc_feature
<222> LOCATION: (1)...(42)
<223> OTHER INFORMATION: n = A,T,C or G
<223> OTHER INFORMATION: primer

<400> SEQUENCE: 38
accatatcct gcagagccnn snnsnnsgtt gagagttatg gc                         42

<210> SEQ ID NO 39
<211> LENGTH: 42
<212> TYPE: DNA
<213> ORGANISM: Artificical Sequence
<220> FEATURE:
<221> NAME/KEY: misc_feature
<222> LOCATION: (1)...(42)
<223> OTHER INFORMATION: n = A,T,C or G
<223> OTHER INFORMATION: primer

<400> SEQUENCE: 39
gccagtgaaa gtgttnnsnn snnsggcaat aattttatgc ac                         42

<210> SEQ ID NO 40

<210> SEQ ID NO 40
<211> LENGTH: 27
<212> TYPE: DNA
<213> ORGANISM: Artificical Sequence
<220> FEATURE:
<223> OTHER INFORMATION: primer

<400> SEQUENCE: 40
gccgccacca tggaggtcca actgcag                               27

<210> SEQ ID NO 41
<211> LENGTH: 31
<212> TYPE: DNA
<213> ORGANISM: Artificical Sequence
<220> FEATURE:
<223> OTHER INFORMATION: primer

<400> SEQUENCE: 41
atgatgtgcg gccgctttta tttccagctt g                          31

<210> SEQ ID NO 42
<211> LENGTH: 25
<212> TYPE: DNA
<213> ORGANISM: Artificical Sequence
<220> FEATURE:
<223> OTHER INFORMATION: primer

<400> SEQUENCE: 42
ggcgcatatg catgtccaac tgcag                                 25

<210> SEQ ID NO 43
<211> LENGTH: 45
<212> TYPE: DNA
<213> ORGANISM: Artificical Sequence
<220> FEATURE:
<223> OTHER INFORMATION: primer

<400> SEQUENCE: 43
agatccgcca ccaccggatc ccctccgcc tgaggagacg gtgac            45

<210> SEQ ID NO 44
<211> LENGTH: 45
<212> TYPE: DNA
<213> ORGANISM: Artificical Sequence
<220> FEATURE:
<223> OTHER INFORMATION: primer

<400> SEQUENCE: 44
ggtggtggcg gatctggagg tggcggcagc ggtaacattg tgctg           45

<210> SEQ ID NO 45
<211> LENGTH: 29
<212> TYPE: DNA
<213> ORGANISM: Artificical Sequence
<220> FEATURE:
<223> OTHER INFORMATION: primer

<400> SEQUENCE: 45
caagctggaa ataaaaaaag cttggcagc                             29

<210> SEQ ID NO 46
<211> LENGTH: 54
<212> TYPE: DNA
<213> ORGANISM: Artificical Sequence
<220> FEATURE:
<223> OTHER INFORMATION: DMab14 hotspot

<400> SEQUENCE: 46
gagattaatc ctagcaacgg tggtggtaac tataatgaga agttcaagag caag        54

<210> SEQ ID NO 47
<211> LENGTH: 18
<212> TYPE: PRT
<213> ORGANISM: Artificial Sequence
<220> FEATURE:
<223> OTHER INFORMATION: DMab14 hotspot

<400> SEQUENCE: 47

Glu Ile Asn Pro Ser Asn Gly Arg Thr Asn Tyr Asn Glu Lys Phe Lys
 1               5                  10                  15

Ser Lys

<210> SEQ ID NO 48
<211> LENGTH: 45
<212> TYPE: DNA
<213> ORGANISM: Artificial Sequence
<220> FEATURE:
<223> OTHER INFORMATION: DMab14 hotspot

<400> SEQUENCE: 48
agagccagtg aaagtgttga gagttatggc aataatttta tgcac                   45

<210> SEQ ID NO 49
<211> LENGTH: 15
<212> TYPE: PRT
<213> ORGANISM: Artificial Sequence
<220> FEATURE:
<223> OTHER INFORMATION: DMab14 hotspot

<400> SEQUENCE: 49

Arg Ala Ser Glu Ser Val Glu Ser Tyr Gly Asn Asn Phe Met His
 1               5                  10                  15

<210> SEQ ID NO 50
<211> LENGTH: 18
<212> TYPE: PRT
<213> ORGANISM: Artificial Sequence
<220> FEATURE:
<223> OTHER INFORMATION: DMab14 wild type or mutant sequence of VH CDR1
     or VL CDR2

<400> SEQUENCE: 50

Glu Ile Asn Pro Ser Asn Gly Arg Thr Asn Tyr Asn Glu Lys Phe Lys
 1               5                  10                  15

Ser Lys

<210> SEQ ID NO 51
<211> LENGTH: 18
<212> TYPE: PRT
<213> ORGANISM: Artificial Sequence
<220> FEATURE:
<223> OTHER INFORMATION: sequence of VH CDR1 or VL CDR2

<400> SEQUENCE: 51

Glu Ile Asn Pro Met Asp Ser Arg Thr Asn Tyr Asn Glu Lys Phe Lys
 1               5                  10                  15

Ser Lys

<210> SEQ ID NO 52
<211> LENGTH: 18
<212> TYPE: PRT
<213> ORGANISM: Artificial Sequence

```
<220> FEATURE:
<223> OTHER INFORMATION: sequence of VH CDR1 or VL CDR2

<400> SEQUENCE: 52

Glu Ile Asn Pro Leu Pro Pro Arg Thr Asn Tyr Asn Glu Lys Phe Lys
 1               5                  10                  15

Ser Lys

<210> SEQ ID NO 53
<211> LENGTH: 15
<212> TYPE: PRT
<213> ORGANISM: Artificial Sequence
<220> FEATURE:
<223> OTHER INFORMATION: sequence of VH CDR1 or VL CDR2

<400> SEQUENCE: 53

Arg Ala Ser Glu Ser Val Glu Ser Tyr Gly Asn Asn Phe Met His
 1               5                  10                  15

<210> SEQ ID NO 54
<211> LENGTH: 15
<212> TYPE: PRT
<213> ORGANISM: Artificial Sequence
<220> FEATURE:
<223> OTHER INFORMATION: sequence of VH CDR1 or VL CDR2

<400> SEQUENCE: 54

Arg Ala Arg Glu Ala Val Glu Ser Tyr Gly Asn Asn Phe Met His
 1               5                  10                  15

<210> SEQ ID NO 55
<211> LENGTH: 15
<212> TYPE: PRT
<213> ORGANISM: Artificial Sequence
<220> FEATURE:
<223> OTHER INFORMATION: sequence of VH CDR1 or VL CDR2

<400> SEQUENCE: 55

Pro Trp Arg Glu Ser Val Glu Ser Tyr Gly Asn Asn Phe Met His
 1               5                  10                  15

<210> SEQ ID NO 56
<211> LENGTH: 15
<212> TYPE: PRT
<213> ORGANISM: Artificial Sequence
<220> FEATURE:
<223> OTHER INFORMATION: sequence of VH CDR1 or VL CDR2

<400> SEQUENCE: 56

Leu Tyr Gly Glu Ser Val Glu Ser Tyr Gly Asn Asn Phe Met His
 1               5                  10                  15

<210> SEQ ID NO 57
<211> LENGTH: 18
<212> TYPE: PRT
<213> ORGANISM: Artificial Sequence
<220> FEATURE:
<223> OTHER INFORMATION: sequence of VH CDR1 or VL CDR2

<400> SEQUENCE: 57

Glu Ile Asn Pro Met Asp Ser Arg Thr Asn Tyr Asn Glu Lys Phe Lys
 1               5                  10                  15

Ser Lys

<210> SEQ ID NO 58
```

-continued

```
<211> LENGTH: 18
<212> TYPE: PRT
<213> ORGANISM: Artificial Sequence
<220> FEATURE:
<223> OTHER INFORMATION: sequence of VH CDR1 or VL CDR2

<400> SEQUENCE: 58

Glu Ile Asn Pro Met Asp Ser Arg Thr Asn Tyr Asn Glu Lys Phe Lys
 1               5                  10                  15

Ser Lys

<210> SEQ ID NO 59
<211> LENGTH: 18
<212> TYPE: PRT
<213> ORGANISM: Artificial Sequence
<220> FEATURE:
<223> OTHER INFORMATION: sequence of VH CDR1 or VL CDR2

<400> SEQUENCE: 59

Glu Ile Asn Pro Met Asp Ser Arg Thr Asn Tyr Asn Glu Lys Phe Lys
 1               5                  10                  15

Ser Lys

<210> SEQ ID NO 60
<211> LENGTH: 18
<212> TYPE: PRT
<213> ORGANISM: Artificial Sequence
<220> FEATURE:
<223> OTHER INFORMATION: sequence of VH CDR1 or VL CDR2

<400> SEQUENCE: 60

Glu Ile Asn Pro Leu Pro Pro Arg Thr Asn Tyr Asn Glu Lys Phe Lys
 1               5                  10                  15

Ser Lys

<210> SEQ ID NO 61
<211> LENGTH: 18
<212> TYPE: PRT
<213> ORGANISM: Artificial Sequence
<220> FEATURE:
<223> OTHER INFORMATION: sequence of VH CDR1 or VL CDR2

<400> SEQUENCE: 61

Glu Ile Asn Pro Leu Pro Pro Arg Thr Asn Tyr Asn Glu Lys Phe Lys
 1               5                  10                  15

Ser Lys

<210> SEQ ID NO 62
<211> LENGTH: 18
<212> TYPE: PRT
<213> ORGANISM: Artificial Sequence
<220> FEATURE:
<223> OTHER INFORMATION: sequence of VH CDR1 or VL CDR2

<400> SEQUENCE: 62

Glu Ile Asn Pro Leu Pro Pro Arg Thr Asn Tyr Asn Glu Lys Phe Lys
 1               5                  10                  15

Ser Lys

<210> SEQ ID NO 63
<211> LENGTH: 15
<212> TYPE: PRT
<213> ORGANISM: Artificial Sequence
<220> FEATURE:
```

<223> OTHER INFORMATION: sequence of VH CDR1 or VL CDR2

<400> SEQUENCE: 63

Arg Ala Arg Glu Ala Val Glu Ser Tyr Gly Asn Asn Phe Met His
 1               5                   10                  15

<210> SEQ ID NO 64
<211> LENGTH: 15
<212> TYPE: PRT
<213> ORGANISM: Artificial Sequence
<220> FEATURE:
<223> OTHER INFORMATION: sequence of VH CDR1 or VL CDR2

<400> SEQUENCE: 64

Pro Trp Arg Glu Ser Val Glu Ser Tyr Gly Asn Asn Phe Met His
 1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: sequence of VH CDR1 or VL CDR2

<400> SEQUENCE: 65

Leu Tyr Gly Glu Ser Val Glu Ser Tyr Gly Asn Asn Phe Met His
 1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: sequence of VH CDR1 or VL CDR2

<400> SEQUENCE: 66

Arg Ala Arg Glu Ala Val Glu Ser Tyr Gly Asn Asn Phe Met His
 1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: sequence of VH CDR1 or VL CDR2

<400> SEQUENCE: 67

Pro Trp Arg Glu Ser Val Glu Ser Tyr Gly Asn Asn Phe Met His
 1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: sequence of VH CDR1 or VL CDR2

<400> SEQUENCE: 68

Leu Tyr Gly Glu Ser Val Glu Ser Tyr Gly Asn Asn Phe Met His
 1               5                   10                  15

<210> SEQ ID NO 69
<211> LENGTH: 4
<212> TYPE: PRT
<213> ORGANISM: Artificial Sequence
<220> FEATURE:
<223> OTHER INFORMATION: fusion protein portion -continued

```
<400> SEQUENCE: 69

Lys Asp Glu Leu
 1

<210> SEQ ID NO 70
<211> LENGTH: 4
<212> TYPE: PRT
<213> ORGANISM: Artificial Sequence
<220> FEATURE:
<223> OTHER INFORMATION: fusion protein portion

<400> SEQUENCE: 70

Arg Asp Glu Leu
 1

<210> SEQ ID NO 71
<211> LENGTH: 9
<212> TYPE: PRT
<213> ORGANISM: Artificial Sequence
<220> FEATURE:
<223> OTHER INFORMATION: linker region

<400> SEQUENCE: 71

Gly Gly Gly Gly Ser Ser Ser Ser Ser
 1               5
```

ANTIBODY FOR 3'-ISOLM1 AND 3',6'-ISO-LD1 GANGLIOSIDES

This application claims the benefit of and incorporates by reference the entire contents of U.S. 61/416,096 filed Nov. 22, 2010, and U.S. 61/419,317 filed Dec. 3, 2010.

The invention was made using funds from the United States government. Therefore, the U.S. government retains certain rights in the invention according to the terms of National Institutes of Health grants 5P50 CA108786, 5P50 NS20023, and R37CA011898.

TECHNICAL FIELD OF THE INVENTION

This invention is related to the area of anti-tumor antibodies. In particular, it relates to antibodies to gangliosides prominently displayed on tumor cell surfaces.

BACKGROUND OF THE INVENTION

Gangliosides are sialic acid-containing glycosphingolipids highly enriched in the vertebrate nervous system. Although their functions have not been fully clarified, they are thought to mediate neural cell-cell recognition and modulate intracellular signaling [1]. Gangliosides are implicated in various neural disorders, primarily the autoimmune neuropathies, but also in storage disorders, e.g. Tay-Sachs disease or Sandhoff disease [2-4]. High-affinity IgG anti-ganglioside antibodies may be used to develop animal models of autoimmune neuropathies and probe normal ganglioside functions. However, it has been difficult to produce high-affinity IgG antibodies against major brain gangliosides, especially GM1, GD1a, and GT1b [5]. This unresponsiveness has been attributed to poor immunogenicity, T-cell independence, and tolerance [5-7]. Advances in genetics provide a potential solution to this problem. Several studies have shown that mice genetically engineered to lack the glycosyltransferase gene for ganglioside synthesis do not express complex gangliosides [8-12]. These mice, immunologically naive to complex gangliosides, have been used for raising new antibodies against complex gangliosides[2, 6, 13, 14].

The Lc3-synthase gene (β1,3-N-acetylglucosaminyltransferase-V: β3Gn-T5) enzyme initiates the formation of the lacto-/neolacto-series ganglioside by transferring GlcNAc in a β1,3-linkage to lactosylceramide (FIG. 1A) [15]. The β3Gn-T5 is detected in mouse development and then again later mainly in the spleen and placenta in adult mice. Additionally, Lc3-synthase transcripts are found in cerebellar Purkinje cells of the adult mouse brain. On the other hand, lacto-series gangliosides such as 3'-isoLM1 and 3',6'-isoLD1 have been reported to be major mono- and oligo-sialogangliosides, respectively, of human gliomas [16-18]. In those studies, monoclonal antibodies (mAbs) such as SL-50, DMab-14, or DMab-22 recognizing lacto-series gangliosides were successfully produced; however, those antibodies proved to be of the low-affinity IgM subclass.

There is a continuing need in the art to obtain high-specificity and high-affinity reagents for treating tumors, especially brain tumors.

SUMMARY OF THE INVENTION

According to one aspect of the invention a monoclonal antibody is provided which has a higher affinity for 3',6'-isoLD1 ganglioside than for 3' isoLM1 ganglioside. Additionally, it does not specifically bind to a ganglioside selected from the group consisting of isoLA1, Fuc3'-isoLM1, 3'-LM1, 3',8'-LD1, Gb3, GA1, GM2, GM1, GD3, GD2, GD1b, and GT1b.

Another aspect of the invention is an IgG monoclonal antibody which binds to one or more lacto-series gangliosides.

Yet another aspect of the invention is an isolated antibody construct which comprises a $V_H$CDR2 according to SEQ ID NO:1 and a $V_L$CDR1 according to SEQ ID NO:2. The antibody construct binds to both 3'-isoLM1 and 3',6'-iso-LD1 gangliosides. The two CDRs can be in the same molecule or in two subunits that heterodimerize.

Yet another aspect of the invention is a hybridoma cell which produces a monoclonal antibody which has a higher affinity for 3',6'-isoLD1 ganglioside than for 3' isoLM1 ganglioside; additionally, it does not specifically bind to a ganglioside selected from the group consisting of isoLA1, Fuc3'-isoLM1, 3'-LM1, 3',8'-LD1, Gb3, GA1, GM2, GM1, GD3, GD2, GD1b, and GT1b. Alternatively, the monoclonal antibody is an IgG monoclonal antibody which binds to one or more lacto-series gangliosides.

Still another aspect of the invention is a method of making a monoclonal antibody. Hybridoma cells are grown in culture. The hybridoma cells produce a monoclonal antibody which has a higher affinity for 3',6'-isoLD1 ganglioside than for 3' isoLM1 ganglioside; additionally, it does not specifically bind to a ganglioside selected from the group consisting of isoLA1, Fuc3'-isoLM1, 3'-LM1, 3',8'-LD1, Gb3, GA1, GM2, GM1, GD3, GD2, GD1b, and GT1b. Alternatively, the hybridoma cells produce an antibody that is an IgG monoclonal antibody which binds to one or more lacto-series gangliosides. Monoclonal antibody is harvested from the culture medium or from the hybridoma cells.

Another aspect of the invention is a method of detecting tumor cells in a tissue. A tissue sample is contacted with a monoclonal antibody which has a higher affinity for 3',6'-isoLD1 ganglioside than for 3' isoLM1 ganglioside; additionally, it does not specifically bind to a ganglioside selected from the group consisting of isoLA1, Fuc3'-isoLM1, 3'-LM1, 3',8'-LD1, Gb3, GA1, GM2, GM1, GD3, GD2, GD1b, and GT1b. Or the tissue sample is contacted with a monoclonal antibody which is an IgG monoclonal antibody which binds to one or more lacto-series gangliosides. Or the tissue sample is contacted with an isolated antibody construct which comprises a $V_H$CDR2 according to SEQ ID NO:1 and a $V_L$CDR1 according to SEQ ID NO:2. The presence of antibody or antibody construct bound to the tissue sample is detected.

Still another aspect of the invention is a method of treating a tumor in a human. An antibody or antibody construct is administered to the human. The antibody has a higher affinity for 3',6'-isoLD1 ganglioside than for 3' isoLM1 ganglioside; additionally, it does not specifically bind to a ganglioside selected from the group consisting of isoLA1, Fuc3'-isoLM1, 3'-LM1, 3',8'-LD1, Gb3, GA1, GM2, GM1, GD3, GD2, GD1b, and GT1b, or the antibody is an IgG monoclonal antibody which binds to one or more lacto-series gangliosides, or the antibody is a construct which comprises a $V_H$CDR2 according to SEQ ID NO:1 and a $V_L$CDR1 according to SEQ ID NO:2. The monoclonal antibody or antibody construct can be attached to a cytotoxic agent.

Another aspect of the invention is an isolated nucleic acid molecule which encodes an scFv molecule comprising a $V_H$CDR2 according to SEQ ID NO:1 and a $V_L$CDR1 according to SEQ ID NO:2. The scFv binds to both 3'-isoLM1 and 3',6'-iso-LD1 gangliosides.

An aspect of the invention is a host cell comprising the isolated nucleic acid which encodes an scFv molecule comprising a $V_H$CDR2 according to SEQ ID NO:1 and a $V_L$CDR1 according to SEQ ID NO:2. The scFv binds to both 3'-isoLM1 and 3',6'-iso-LD1 gangliosides.

A further aspect of the invention is a method of making an antibody construct. The host cell comprising the isolated nucleic acid which encodes an scFv molecule comprising a $V_H$CDR2 according to SEQ ID NO:1 and a $V_L$CDR1 according to SEQ ID NO:2, wherein the scFv binds to both 3'-isoLM1 and 3',6'-iso-LD1 gangliosides is grown in culture medium. The antibody construct is harvested from the culture medium or the host cells.

These and other embodiments which will be apparent to those of skill in the art upon reading the specification provide the art with new reagents for treating and directing treatments to tumors.

BRIEF DESCRIPTION OF THE DRAWINGS

(FIG. 1A) Biosynthesis of lacto-/neolacto-series ganglioside. (FIG. 1B) Electrophoresis of 2 μg of GMab-1 under reducing conditions on 4-10% NuPAGE gel. (FIG. 1C) ELISA of GMab-1 against 3'-isoLM1. The 3'-isoLM1 conjugated with BSA was immobilized. After blocking, the plates were incubated with GMab-1 and isotype control at several concentrations.

FIG. 5. Sequence alignment of DMab14-scFv (SEQ ID NOS: 9, 7, 10, 8) and DMab14-86184 (SEQ ID NOs: 3, 1, 4, 2) in VHCDR2 (SEQ ID NOS: 10, 8, 4, 2, top to bottom) and VLCDR1 (SEQ ID NOS: 9, 7, 3, 1, top to bottom) regions. Differences are noted.

FIG. 6. DMab14-86184-scFv (VH-Linker-VL construction) nucleotide (SEQ ID NO:5) and amino acid (SEQ ID NO:6) sequence, G4S×3 linker at amino acid residues approximately 161-175.

DETAILED DESCRIPTION OF THE INVENTION

Figure 1A:
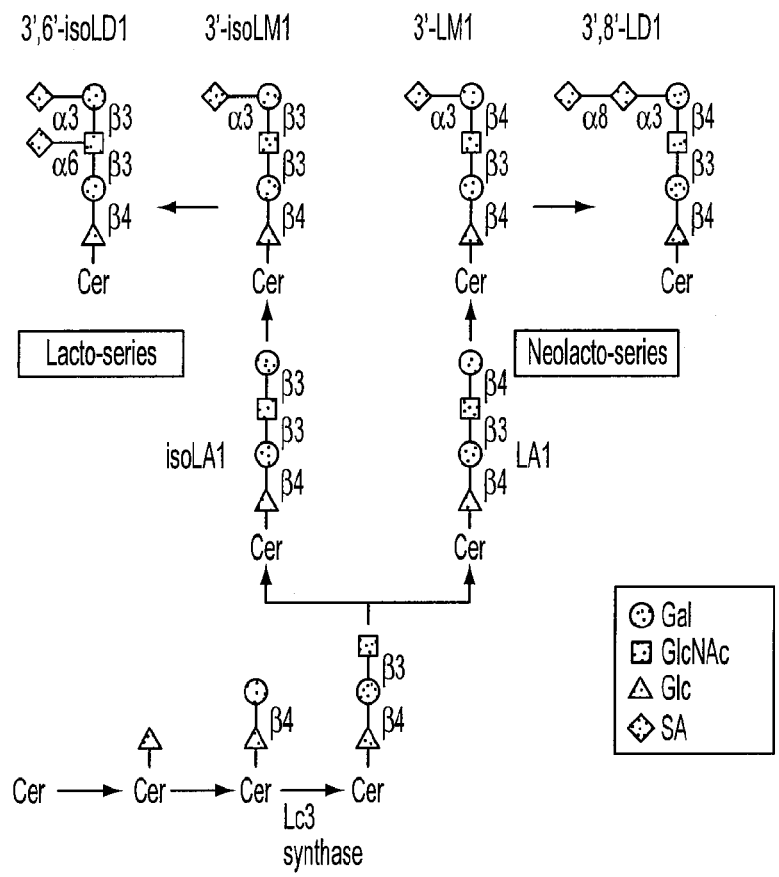
FIG. 1A-1C. Production of an anti-3'-isoLM1/3',6'-isoLD1 ganglioside antibody.

The inventors have developed antibodies (monoclonal or scFv construct) that have unique epitopic specificity for gangliosides and which have high affinity. The ganglioside targets of the antibody are found on the cell surfaces of certain tumors. This renders the antibodies useful reagents for treating tumors and for delivering anti-tumor reagents to tumors. Additionally the antibodies can be used analytically, prophylactically, prognostically, diagnostically, therapeutically, and theranostically.

The antibodies of the invention may be produced using hybridoma cells. Hybridoma cells can be cultured and the monoclonal antibodies can be harvested from the culture medium or from the hybridoma cells.

One epitope to which the antibodies may bind is NeuAcα2-3Galβ1-3GlcNAc. The antibodies may bind with a higher affinity constant to 3',6'-isoLD1 ganglioside than to 3'-isoLM1 ganglioside. The affinity constant for 3'-isoLM1 ganglioside may be at least $1 \times 10^7$, at least $5 \times 10^7$, at least $10^8$, or at least $5 \times 10^8$ $(mol/L)^{-1}$. The affinity constant for 3',6'-isoLD1 ganglioside will accordingly be higher. The antibodies may not bind to one or more of gangliosides isoLA1, Fuc3'-isoLM1, 3'-LM1, 3',8'-LD1, Gb3, GA1, GM2, GM1, GD3, GD2, GD1b, and GT1b. The antibodies may not bind to any of these gangliosides. Non-binding may be less than 0.05, less than 0.04, less than 0.03, less than 0.02 of the amount of binding to 3'-isoLM1 ganglioside.

The isotype of the antibodies is IgG. It may be any of IgG1, IgG2, IgG3, or IgG4 subtypes. Other types of antibodies may also be used if they can achieve sufficient binding affinities as shown here. Typically such binding affinities are at least $1 \times 10^7$, at least $5 \times 10^7$, at least $10^8$, or at least $5 \times 10^8$ $(mol/L)^{-1}$ for 3'-isoLM1 ganglioside. In some cases other types of antibodies can be used and they can be "matured" to increase their affinity. Such maturation typically involves rounds of selection for binding-beneficial mutations. Other strategies for maturation can be used, including designing changes, rather than selecting among random changes.

Antibodies can be purified by methods well known in the art. For example, antibodies can be affinity purified by passage over a column to which the relevant antigen is bound. The bound antibodies can then be eluted from the column using a buffer with a high salt concentration.

Hybridomas which produce desired anti-ganglioside antibodies can be propagated in vitro as is known in the art to provide a long-lasting source of antibodies. Alternatively, hybridoma cells can be injected intraperitoneally into mice, which will then produce tumors. These tumors are accompanied by the production of ascites fluid which contains the desired monoclonal antibodies. The monoclonal antibodies can be recovered from the ascites fluid by conventional methods such as ultrafiltration, ultracentrifugation, dialysis, and immunoaffinity chromatography.

Single-chain antibodies can be constructed, for example, using hybridoma cDNA as a template and a DNA amplification method, such as PCR (Thirion et al., 1996, Eur. J. Cancer Prev. 5, 507-11). Single-chain antibodies can be mono- or bispecific, and can be bivalent or tetravalent. Construction of tetravalent, bispecific single-chain antibodies is taught, for example, in Coloma & Morrison, 1997, Nat. Biotechnol. 15, 159-63. Construction of bivalent, bispecific single-chain antibodies is taught in Mallender & Voss, 1994, J. Biol. Chem. 269, 199-206. As a non-limiting example of such a construct see SEQ ID NO:5 and 6.

A nucleotide sequence encoding a single-chain antibody can be constructed using manual or automated nucleotide synthesis, cloned into an expression construct using standard recombinant DNA methods, and introduced into a cell to express the coding sequence, as described below. Alternatively, single-chain antibodies can be produced directly using, for example, filamentous phage technology (Verhaar et al., 1995, Int. J. Cancer 61, 497-501; Nicholls et al., 1993, J. Immunol. Meth. 165, 81-91).

The presence of antibody (indicating the presence of analyte) can be detected, analytically, in a body sample, such as a tissue or body fluid, for example. The antibody can be labeled before contacting with a sample, for example, with a radionuclide or an enzyme. Alternatively the antibody is initially unlabeled, and after contacting it is labeled by use of a second antibody which recognizes the type of the first antibody. The second antibody may be detectably labeled. Such detection systems are well known in the art. The format of the assay can be any that is known in the art. The antibody can be used in immunohistochemistry, or in an ELISA format, for example. The antibody can be used in a fluorescence activated cell sorter. Many different techniques and formats for detecting bound antibody are known and can be used. Antibodies can be attached to solid supports, such as wells, arrays, beads, and microspheres.

Any toxic moiety can be attached to the antibodies to achieve delivery of the toxic moiety to the appropriate site in the body, typically the site of the tumor. One such toxin which can be used is *Pseudomonas* exotoxin (PE38). Other suitable therapeutic agents include small molecule cytotoxic agents, i.e., compounds with the ability to kill mammalian cells and having a molecular weight of less than 700 daltons. Such compounds may also contain toxic metals capable of having a cytotoxic effect. Such small molecule cytotoxic agents include pro-drugs, i.e., compounds that decay or are converted under physiological conditions to release cytotoxic agents. Examples of such agents include cisplatin, maytansine derivatives, rachelmycin, calicheamicin, docetaxel, etoposide, gemcitabine, ifosfamide, irinotecan, melphalan, mitoxantrone, sorfimer sodiumphotofrin II, temozolmide, topotecan, trimetreate glucuronate, auristatin E vincristine and doxorubicin. Other toxic moieties which may be used are peptide cytotoxins, i.e., proteins or fragments of proteins that have the ability to kill mammalian cells. Examples include ricin, diphtheria toxin, *Pseudomonas* bacterial exotoxin A, DNAase and RNAase. Additional toxic moieties that may be used are radionuclides, i.e., unstable isotopes of elements which decay thereby emitting one or more of $\alpha$ or $\beta$ particles, or $\gamma$ rays. Examples include iodine 131, rhenium 186, indium 111, yttrium 90, bismuth 210 and 213, actinium 225 and astatine 213. Means for attaching, conjugating, binding, complexing, and chelating toxic moieties to antibodies are well known in the art. A method that is appropriate for the agent and the use of the antibody can be chosen readily by the skilled artisan.

The antibodies are useful for treating, alone or as part of a combination treatment, a variety of tumors. These include but are not limited to brain tumors such as glioblastoma, breast, prostate, colon, renal cell, pancreas, melanoma, seminoma, germinoma, teratoma, and leiomyosarcoma. Not all tumors may express the targeted gangliosides. Tumor cells which do express the targeted gangliosides on their surfaces are likely more susceptible than those which do not. Thus one may want to pre-screen patients to be treated by testing their tumor cells for expression, and preferably robust expression, of the targeted gangliosides. Thus, a treatment can be personalized and unnecessary treatments can be avoided. Thus unnecessary expense and possible side effects can be avoided.

Definitions

Units, prefixes, and symbols are denoted in their Systeme International de Unites (SI) accepted form. Numeric ranges are inclusive of the numbers defining the range. Unless otherwise indicated, nucleic acids are written left to right in 5' to 3' orientation; amino acid sequences are written left to right in amino to carboxy orientation. The headings provided herein are not limitations of the various aspects or embodiments of the disclosure which can be had by reference to the specification as a whole. Accordingly, the terms defined immediately below are more fully defined by reference to the specification in its entirety.

The term "ganglioside" refers to those sialylated glycosphingolipids which constitute the major class of glycoconjugates on neurons and carry the majority of the sialic acid within the central nervous system. Gangliosides, a group of the glioma-associated antigens, are believed to play a role in tumor formation and significantly impact tumor progression. They are involved in various cellular functions, including signal transduction, regulation of cell proliferation and differentiation, cell-cell regulation and adhesion, and cell death (see, e.g., Hwang, L. et al. 2010). In preferred embodiments, the term "gangliosides" refers to 3' iso-LM1 and/or 3'6' iso-LD1, both of which have been characterized and validated as molecular targets for the treatment of malignant gliomas because of their overexpression in those tumors, especially glioblastoma multiforme (see, e.g., Wikstrand, Fredman et al., 1992; Fredman 1994).

As used herein, "antibody" includes reference to an immunoglobulin molecule immunologically reactive with a particular antigen, and includes both polyclonal and monoclonal antibodies. The term also includes genetically engineered forms such as chimeric antibodies (e.g., humanized murine antibodies), heteroconjugate antibodies (e.g., bispecific antibodies) and recombinant single chain Fv fragments (scFv), disulfide stabilized (dsFv) Fv fragments (See, U.S. Ser. No. 08/077,252, incorporated herein by reference), or pFv fragments (See, U.S. Provisional Patent Applications 60/042,350 and 60/048,848, both of which are incorporated herein by reference.). The term "antibody" also includes antigen binding forms of antibodies (e.g., Fab', F(ab')$_2$, Fab, Fv and rIgG (See also, Pierce Catalog and Handbook, 1994-1995 (Pierce Chemical Co., Rockford, Ill.).

An antibody immunologically reactive with a particular antigen can be generated by recombinant methods such as selection of libraries of recombinant antibodies in phage or similar vectors (See, e.g., Huse, et al., Science 246:1275-1281 (1989); Ward, et al., Nature 341:544-546 (1989); and Vaughan, et al., Nature Biotech. 14:309-314 (1996)).

Typically, an immunoglobulin has a heavy and light chain. Each heavy and light chain contains a constant region and a variable region. Light and heavy chain variable regions contain a "framework" region interrupted by three hypervariable regions, also called complementarity-determining regions or CDRs. The extent of the framework region and CDRs have been defined (see, SEQUENCES OF PROTEINS OF IMMUNOLOGICAL INTEREST, Kabat, E., et al., U.S. Department of Health and Human Services, (1987); which is incorporated herein by reference). The sequences of the framework regions of different light or heavy chains are relatively conserved within a species. The framework region of an antibody, that is the combined framework regions of the constituent light and heavy chains, serves to position and align the CDRs in three dimensional space. The CDRs are primarily responsible for binding to an epitope of an antigen. The CDRs are typically referred to as CDR1, CDR2, and CDR3, numbered sequentially starting from the N-terminus.

The phrase "single chain Fv" or "scFv" refers to an antibody in which the heavy chain and the light chain of a traditional two chain antibody have been joined to form one chain. Typically, a linker peptide is inserted between the two chains to allow for proper folding and creation of an active binding site.

The term "linker peptide" includes reference to a peptide within an antibody binding fragment (e.g., Fv fragment) which serves to indirectly bond the variable heavy chain to the variable light chain.

The term "contacting" includes reference to placement in direct physical association. With regards to this invention, the term refers to antibody-antigen binding.

As used herein, the term "anti-ganglioside" in reference to an antibody, includes reference to an antibody which is generated against ganglioside, such as 3' isoLM1 and 3'6' isoLD1. In certain embodiments, the ganglioside is a primate ganglioside such as human ganglioside. In other embodiments, the antibody is generated against human ganglioside synthesized by a non-primate mammal after introduction into the animal of cDNA which encodes human ganglioside.

As used herein, "polypeptide", "peptide" and "protein" are used interchangeably and include reference to a polymer of amino acid residues. The terms apply to amino acid polymers in which one or more amino acid residue is an artificial chemical analogue of a corresponding naturally occurring amino acid, as well as to naturally occurring amino acid polymers. The terms also apply to polymers containing conservative amino acid substitutions such that the protein remains functional.

The term "residue" or "amino acid residue" or "amino acid" includes reference to an amino acid that is incorporated into a protein, polypeptide, or peptide (collectively "peptide"). The amino acid can be a naturally occurring amino acid and, unless otherwise limited, can encompass known analogs of natural amino acids that can function in a similar manner as naturally occurring amino acids.

The phrase "disulfide bond" or "cysteine-cysteine disulfide bond" refers to a covalent interaction between two cysteines in which the sulfur atoms of the cysteines are oxidized to form a disulfide bond. The average bond energy of a disulfide bond is about 60 kcal/mol compared to 1-2 kcal/mol for a hydrogen bond. In the context of this invention, the cysteines which form the disulfide bond are within the framework regions of the single chain antibody and serve to stabilize the conformation of the antibody.

The terms "conjugating," "joining," "bonding" or "linking" refer to making two polypeptides into one contiguous polypeptide molecule. In the context of the present invention, the terms include reference to joining an antibody moiety to an effector molecule (EM). The linkage can be either by chemical or recombinant means. Chemical means refers to a reaction between the antibody moiety and the effector molecule such that there is a covalent bond formed between the two molecules to form one molecule.

As used herein, "recombinant" includes reference to a protein produced using cells that do not have, in their native state, an endogenous copy of the DNA able to express the protein. The cells produce the recombinant protein because they have been genetically altered by the introduction of the appropriate isolated nucleic acid sequence. The term also includes reference to a cell, or nucleic acid, or vector, that has been modified by the introduction of a heterologous nucleic acid or the alteration of a native nucleic acid to a form not native to that cell, or that the cell is derived from a cell so modified. Thus, for example, recombinant cells express genes that are not found within the native (non-recombinant) form of the cell, express mutants of genes that are found within the native form, or express native genes that are otherwise abnormally expressed, under expressed or not expressed at all.

As used herein, "nucleic acid" or "nucleic acid sequence" includes reference to a deoxyribonucleotide or ribonucleotide polymer in either single- or double-stranded form, and unless otherwise limited, encompasses known analogues of natural nucleotides that hybridize to nucleic acids in a manner similar to naturally occurring nucleotides. Unless otherwise indicated, a particular nucleic acid sequence includes the complementary sequence thereof as well as conservative variants, i.e., nucleic acids present in wobble positions of codons and variants that, when translated into a protein, result in a conservative substitution of an amino acid.

As used herein, "encoding" with respect to a specified nucleic acid, includes reference to nucleic acids which comprise the information for translation into the specified protein. The information is specified by the use of codons. Typically, the amino acid sequence is encoded by the nucleic acid using the "universal" genetic code. However, variants of the universal code, such as is present in some plant, animal, and fungal mitochondria, the bacterium *Mycoplasma capricolumn* (Proc. Nat'l Acad. Sci. USA 82:2306-2309 (1985), or the ciliate Macronucleus, may be used when the nucleic acid is expressed in using the translational machinery of these organisms.

The phrase "fusing in frame" refers to joining two or more nucleic acid sequences which encode polypeptides so that the joined nucleic acid sequence translates into a single chain protein which comprises the original polypeptide chains.

As used herein, "expressed" includes reference to translation of a nucleic acid into a protein. Proteins may be expressed and remain intracellular, become a component of the cell surface membrane or be secreted into the extracellular matrix or medium.

By "host cell" is meant a cell which can support the replication or expression of the expression vector. Host cells may be prokaryotic cells such as *E. coli*, or eukaryotic cells such as yeast, insect, amphibian, or mammalian cells.

The phrase "phage display library" refers to a population of bacteriophage, each of which contains a foreign cDNA recombinantly fused in frame to a surface protein. The phage displays the foreign protein encoded by the cDNA on its surface. After replication in a bacterial host, typically *E. coli*, the phage which contain the foreign cDNA of interest are selected by the expression of the foreign protein on the phage surface.

The terms "effective amount" or "amount effective to" or "therapeutically effective amount" include reference to a dosage of a therapeutic agent sufficient to produce a desired result, such as inhibiting cell protein synthesis by at least 50%, or killing the cell.

The term "therapeutic agent" includes any number of compounds currently known or later developed to act as anti-neoplastics, anti-inflammatories, cytokines, anti-infectives, enzyme activators or inhibitors, allosteric modifiers, antibiotics or other agents administered to induce a desired therapeutic effect in a patient.

The term "immunoconjugate" includes reference to a covalent linkage of an effector molecule to an antibody. The effector molecule can be an immunotoxin.

The term "toxin" includes reference to abrin, ricin, Pseudomonas exotoxin (PE), diphtheria toxin (DT), botulinum toxin, or modified toxins thereof. For example, PE and DT are highly toxic compounds that typically bring about death through liver toxicity. PE and DT, however, can be modified into a form for use as an immunotoxin by removing the native targeting component of the toxin (e.g., domain Ia of PE and the B chain of DT) and replacing it with a different targeting moiety, such as an antibody.

The term "in vivo" includes reference to inside the body of the organism from which the cell was obtained. "Ex vivo" and "in vitro" means outside the body of the organism from which the cell was obtained.

The phrase "malignant cell" or "malignancy" refers to tumors or tumor cells that are invasive and/or able to undergo metastasis, i.e., a cancerous cell.

As used herein, "mammalian cells" includes reference to cells derived from mammals including humans, rats, mice, guinea pigs, chimpanzees, or macaques. The cells may be cultured in vivo or in vitro.

The term "selectively reactive" includes reference to the preferential association of an antibody, in whole or part, with a cell or tissue bearing gangliosides and not to cells or tissues lacking gangliosides. It is, of course, recognized that a certain degree of nonspecific interaction may occur between a molecule and a non-target cell or tissue. Nevertheless, selective reactivity, may be distinguished as mediated through specific recognition of gangliosides. Although selectively reactive antibodies bind antigen, they may do so with low affinity. On the other hand, specific binding results in a much stronger association between the antibody and cells bearing gangliosides than between the bound antibody and cells lacking gangliosides or low affinity antibody-antigen binding. Specific binding typically results in greater than 2-fold, preferably greater than 5-fold, more preferably greater than 10-fold and most preferably greater than 100-fold increase in amount of bound antibody (per unit time) to a cell or tissue bearing gangliosides as compared to a cell or tissue lacking gangliosides. Specific binding to a protein under such conditions requires an antibody that is selected for its specificity for a particular protein. A variety of immunoassay formats are appropriate for selecting antibodies specifically immunoreactive with a particular protein. For example, solid-phase ELISA immunoassays are routinely used to select monoclonal antibodies specifically immunoreactive with a protein. See Harlow & Lane, ANTIBODIES, A LABORATORY MANUAL, Cold Spring Harbor Publications, New York (1988), for a description of immunoassay formats and conditions that can be used to determine specific immunoreactivity.

The term "immunologically reactive conditions" includes reference to conditions which allow an antibody generated to a particular epitope to bind to that epitope to a detectably greater degree than, and/or to the substantial exclusion of, binding to substantially all other epitopes. Immunologically reactive conditions are dependent upon the format of the antibody binding reaction and typically are those utilized in immunoassay protocols or those conditions encountered in vivo. See Harlow & Lane, supra, for a description of immunoassay formats and conditions. Preferably, the immunologically reactive conditions employed in the methods of the present disclosure are "physiological conditions" which include reference to conditions (e.g., temperature, osmolarity, pH) that are typical inside a living mammal or a mammalian cell. While it is recognized that some organs are subject to extreme conditions, the intra-organismal and intracellular environment normally lies around pH 7 (i.e., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

The anti-ganglioside antibodies employed in the present disclosure can be linked to effector molecules (EM) through the EM carboxyl terminus, the EM amino terminus, through an interior amino acid residue of the EM such as cysteine, or any combination thereof. Similarly, the EM can be linked directly to the heavy, light, Fc (constant region) or framework regions of the antibody. Linkage can occur through the antibody's amino or carboxyl termini, or through an interior amino acid residue. Further, multiple EM molecules (e.g., any one of from 2-10) can be linked to the anti-ganglioside antibody and/or multiple antibodies (e.g., any one of from 2-5) can be linked to an EM. The antibodies used in a multivalent immunoconjugate composition of the present invention can be directed to the same or different ganglioside epitopes.

In certain embodiments of the present disclosure, the anti-ganglioside antibody is a recombinant antibody such as a scFv or disulfide stabilized Fv antibody. Fv antibodies are typically about 25 kDa and contain a complete antigen-binding site with 3 CDRs per heavy and light chain. If the $V_H$ and the $V_L$ chain are expressed non-contiguously, the chains of the Fv antibody are typically held together by noncovalent interactions. However, these chains tend to dissociate upon dilution, so methods have been developed to crosslink the chains through glutaraldehyde, intermolecular disulfides, or a peptide linker.

In other embodiments, the antibody is a single chain Fv (scFv). The $V_H$ and the $V_L$ regions of a scFv antibody comprise a single chain which is folded to create an antigen binding site similar to that found in two-chain antibodies. Once folded, noncovalent interactions stabilize the single chain antibody. In certain embodiments, the scFv is recombinantly produced. One of skill will realize that conservative variants of the antibodies of the instant invention can be made. Such conservative variants employed in scFv fragments will retain critical amino acid residues necessary for correct folding and stabilizing between the $V_H$ and the $V_L$ regions. Conservatively modified variants of the prototype sequence have at least 80% sequence similarity, preferably at least 85% sequence similarity, more preferably at least 90% sequence similarity, and most preferably at least 95% sequence similarity at the amino acid level to its prototype sequence.

In some embodiments of the present invention, the scFv antibody is directly linked to the EM through the light chain. However, scFv antibodies can be linked to the EM via its amino or carboxyl terminus.

While the $V_H$ and $V_L$ regions of some antibody embodiments can be directly joined together, one of skill will appreciate that the regions may be separated by a peptide linker consisting of one or more amino acids. Peptide linkers and their use are well-known in the art. See, e.g., Huston, et al., Proc. Nat'l Acad. Sci. USA 8:5879 (1988); Bird, et al., Science 242:4236 (1988); Glockshuber, et al., Biochemistry 29:1362 (1990); U.S. Pat. No. 4,946,778, U.S. Pat. No. 5,132,405 and Stemmer, et al., Biotechniques 14:256-265 (1993), all incorporated herein by reference. Generally the peptide linker will have no specific biological activity other than to join the regions or to preserve some minimum distance or other spatial relationship between them. However, the constituent amino acids of the peptide linker may be selected to influence some property of the molecule such as the folding, net charge, or hydrophobicity. Single chain Fv (scFv) antibodies optionally include a peptide linker of no more than 50 amino acids, generally no more than 40 amino acids, preferably no more than 30 amino acids, and more preferably no more than 20 amino acids in length. However, it is to be appreciated that some amino acid substitutions within the linker can be made. For example, a valine can be substituted for a glycine.

Antibody Production

Methods of producing polyclonal antibodies are known to those of skill in the art. In brief, an immunogen, preferably isolated ganglioside or extracellular ganglioside epitopes are mixed with an adjuvant and animals are immunized with the mixture. When appropriately high titers of antibody to the immunogen are obtained, blood is collected from the animal and antisera are prepared. If desired, further fractionation of the antisera to enrich for antibodies reactive to the polypeptide is performed. See, e.g., Coligan, CURRENT PROTOCOLS IN IMMUNOLOGY, Wiley/Greene, NY (1991); and Harlow & Lane, supra, which are incorporated herein by reference.

Monoclonal antibodies may be obtained by various techniques familiar to those skilled in the art. Description of techniques for preparing such monoclonal antibodies may be found in, e.g., Stites, et al. (eds.) BASIC AND CLINICAL IMMUNOLOGY (4TH ED.), Lange Medical Publications, Los Altos, Calif., and references cited therein; Harlow & Lane, supra; Goding, MONOCLONAL ANTIBODIES: PRINCIPLES AND PRACTICE (2D ED.), Academic Press, New York, N.Y. (1986); Kohler & Milstein, Nature 256: 495-497 (1975); and particularly (Chowdhury, P. S., et al., Mol. Immunol. 34:9 (1997)), which discusses one method of generating monoclonal antibodies.

Binding Affinity of Antibodies

The antibodies of this disclosure specifically bind to an extracellular epitope of ganglioside. An anti-ganglioside antibody has binding affinity for ganglioside if the antibody binds or is capable of binding ganglioside as measured or determined by standard antibody-antigen assays, for example, competitive assays, saturation assays, or standard immunoassays such as ELISA or RIA.

Such assays can be used to determine the dissociation constant of the antibody. The phrase "dissociation constant" refers to the affinity of an antibody for an antigen. Specificity of binding between an antibody and an antigen exists if the dissociation constant ($k_D$=1/K, where K is the affinity constant) of the antibody is <1 µM, preferably <100 nM, and most preferably <0.1 nM. Antibody molecules will typically have a $k_D$ in the lower ranges. $k_D$=[Ab–Ag]/[Ab][Ag] where [Ab] is the concentration at equilibrium of the antibody, [Ag] is the concentration at equilibrium of the antigen and [Ab–Ag] is the concentration at equilibrium of the antibody-antigen complex. Typically, the binding interactions between antigen and antibody include reversible noncovalent associations such as electrostatic attraction, Van der Waals forces and hydrogen bonds. This method of defining binding specificity applies to single heavy and/or light chains, CDRs, fusion proteins or fragments of heavy and/or light chains, that are specific for ganglioside if they bind ganglioside alone or in combination.

Production of Immunoconjugates

Immunoconjugates include, but are not limited to, molecules in which there is a covalent linkage of a therapeutic agent to an antibody. A therapeutic agent is an agent with a particular biological activity directed against a particular target molecule or a cell bearing a target molecule. One of skill in the art will appreciate that therapeutic agents may include various drugs such as vinblastine, daunomycin and the like, cytotoxins such as native or modified *Pseudomonas* exotoxin or Diphtheria toxin, encapsulating agents, (e.g., liposomes) which themselves contain pharmacological compositions, radioactive agents such as $^{125}$I, $^{32}$P, $^{14}$C, $^{3}$H and $^{35}$S and other labels, target moieties and ligands.

The choice of a particular therapeutic agent depends on the particular target molecule or cell and the biological effect is desired to evoke. Thus, for example, the therapeutic agent may be a cytotoxin which is used to bring about the death of a particular target cell. Conversely, where it is merely desired to invoke a non-lethal biological response, the therapeutic agent may be conjugated to a non-lethal pharmacological agent or a liposome containing a non-lethal pharmacological agent.

With the therapeutic agents and antibodies herein provided, one of skill can readily construct a variety of clones containing functionally equivalent nucleic acids, such as nucleic acids which differ in sequence but which encode the same EM or antibody sequence. Thus, the present invention provides nucleic acids encoding antibodies and conjugates and fusion proteins thereof.

*Pseudomonas* Exotoxin and Other Toxins

Toxins can be employed with antibodies of the present disclosure to yield immunotoxins. Exemplary toxins include ricin, abrin, diphtheria toxin and subunits thereof, as well as botulinum toxins A through F. These toxins are readily available from commercial sources (e.g., Sigma Chemical Company, St. Louis, Mo.). Diptheria toxin is isolated from *Corynebacterium diphtheriae*. Ricin is the lectin RCA60 from *Ricinus communis* (Castor bean). The term also references toxic variants thereof. For example, see, U.S. Pat. Nos. 5,079,163 and 4,689,401. *Ricinus communis* agglutinin (RCA) occurs in two forms designated RCA.sub.60 and RCA.sub.120 according to their molecular weights of approximately 65 and 120 $k_D$ respectively (Nicholson & Blaustein, J. Biochim. Biophys. Acta 266:543 (1972)). The A chain is responsible for inactivating protein synthesis and killing cells. The B chain binds ricin to cell-surface galactose residues and facilitates transport of the A chain into the cytosol (Olsnes, et al., Nature 249:627-631 (1974) and U.S. Pat. No. 3,060,165).

Abrin includes toxic lectins from *Abrus precatorius*. The toxic principles, abrin a, b, c, and d, have a molecular weight of from about 63 and 67 $k_D$ and are composed of two disulfide-linked polypeptide chains A and B. The A chain inhibits protein synthesis; the B-chain (abrin-b) binds to D-galactose residues (see, Funatsu, et al., Agr. Biol. Chem. 52:1095 (1988); and Olsnes, Methods Enzymol. 50:330-335 (1978)).

In preferred embodiments of the present disclosure, the toxin is *Pseudomonas* exotoxin (PE). The term "*Pseudomonas* exotoxin" as used herein refers to a full-length native (naturally occurring) PE or a PE that has been modified. Such modifications may include, but are not limited to, elimination of domain Ia, various amino acid deletions in domains Ib, II and III, single amino acid substitutions and the addition of one or more sequences at the carboxyl terminus such as KDEL (SEQ ID NO: 69) and REDL (SEQ ID NO: 70). See Siegall et al., J. Biol. Chem. 264:14256 (1989). In a preferred embodiment, the cytotoxic fragment of PE retains at least 50%, preferably 75%, more preferably at least 90%, and most preferably 95% of the cytotoxicity of native PE. In a most preferred embodiment, the cytotoxic fragment is more toxic than native PE.

Native *Pseudomonas* exotoxin A (PE) is an extremely active monomeric protein (molecular weight 66 kD), secreted by *Pseudomonas aeruginosa*, which inhibits protein synthesis in eukaryotic cells. The native PE sequence is provided as SEQ ID NO:1 of U.S. Pat. No. 5,602,095, incorporated herein by reference. The method of action is inactivation of the ADP-ribosylation of elongation factor 2 (EF-2). The exotoxin contains three structural domains that act in concert to cause cytotoxicity. Domain Ia (amino acids 1-252) mediates cell binding. Domain II (amino acids 253-364) is responsible for translocation into the cytosol and domain III (amino acids 400-613) mediates ADP ribosylation of elongation factor 2. The function of domain Ib (amino acids 365-399) remains undefined, although a large part of it, amino acids 365-380, can be deleted without loss of cytotoxicity. See Siegall, et al., J. Biol. Chem. 264: 14256-14261 (1989), incorporated by reference herein.

PE employed in the present invention include the native sequence, cytotoxic fragments of the native sequence, and conservatively modified variants of native PE and its cytotoxic fragments. Cytotoxic fragments of PE include those which are cytotoxic with or without subsequent proteolytic or other processing in the target cell (e.g., as a protein or pre-protein). Cytotoxic fragments of PE include PE40, PE38, and PE35. PE40 is a truncated derivative of PE as previously described in the art. See, Pai, et al., Proc. Nat'l Acad. Sci. USA 88:3358-62 (1991); and Kondo, et al., J. Biol. Chem. 263:9470-9475 (1988). PE35 is a 35 $K_D$ carboxyl-terminal fragment of PE composed of a met at position 280 followed by amino acids 281-364 and 381-613 of native PE. In other embodiments, the cytotoxic fragment PE38 is employed. PE38 is a truncated PE pro-protein composed of amino acids 253-364 and 381-613 which is activated to its cytotoxic form upon processing within a cell (see U.S. Pat. No. 5,608,039, incorporated herein by reference).

In certain embodiment, PE38 is the toxic moiety of the immunotoxin of this disclosure, however, other cytotoxic fragments PE35 and PE40 are contemplated and are disclosed in U.S. Pat. Nos. 5,602,095 and 4,892,827, each of which is incorporated herein by reference.

Other Therapeutic Moieties

Antibodies of the present disclosure can also be used to target any number of different diagnostic or therapeutic compounds to cells expressing ganglioside on their surface. Thus, an antibody of the present invention, such as an anti-ganglioside scFv, may be attached directly or via a linker to a drug that is to be delivered directly to cells bearing ganglioside. Therapeutic agents include such compounds as nucleic acids, proteins, peptides, amino acids or derivatives, glycoproteins, radioisotopes, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides.

Alternatively, the molecule linked to an anti-ganglioside antibody may be an encapsulation system, such as a liposome or micelle that contains a therapeutic composition such as a drug, a nucleic acid (e.g. an antisense nucleic acid), or another therapeutic moiety that is preferably shielded from direct exposure to the circulatory system. Means of preparing liposomes attached to antibodies are well known to those of skill in the art. See, for example, U.S. Pat. No. 4,957,735; and Connor, et al., Pharm. Ther. 28:341-365 (1985).

Detectable Labels

Antibodies of the present disclosure may optionally be covalently or noncovalently linked to a detectable label. Detectable labels suitable for such use include any composition detectable by spectroscopic, photochemical, biochemical, immunochemical, electrical, optical or chemical means. Useful labels in the present invention include magnetic beads (e.g. DYNABEADS™ superparamagnetic particles), fluorescent dyes (e.g., fluorescein isothiocyanate, TEXAS RED™ bright-red, fluorescent dye, rhodamine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic (e.g. polystyrene, polypropylene, latex, etc.) beads.

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

Conjugation to the Antibody

In a non-recombinant embodiment of the invention, effector molecules, e.g., therapeutic, diagnostic, or detection moieties, are linked to the anti-ganglioside antibodies of the present disclosure using any number of means known to those of skill in the art. Both covalent and noncovalent attachment means may be used with anti-ganglioside antibodies of the present disclosure.

The procedure for attaching an effector molecule to an antibody will vary according to the chemical structure of the EM. Polypeptides typically contain variety of functional groups; e.g., carboxylic acid (COOH), free amine (—NH$_2$) or sulfhydryl (—SH) groups, which are available for reaction with a suitable functional group on an antibody to result in the binding of the effector molecule.

Alternatively, the antibody is derivatized to expose or attach additional reactive functional groups. The derivatization may involve attachment of any of a number of linker molecules such as those available from Pierce Chemical Company, Rockford Ill.

A "linker", as used herein, is a molecule that is used to join the antibody to the effector molecule. The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (e.g., through a disulfide linkage to cysteine). However, in certain embodiments, the linkers will be joined to the alpha carbon amino and carboxyl groups of the terminal amino acids.

In some circumstances, it is desirable to free the effector molecule from the antibody when the immunoconjugate has reached its target site. Therefore, in these circumstances, immunoconjugates will comprise linkages which are cleavable in the vicinity of the target site. Cleavage of the linker to release the effector molecule from the antibody may be prompted by enzymatic activity or conditions to which the immunoconjugate is subjected either inside the target cell or in the vicinity of the target site. When the target site is a tumor, a linker which is cleavable under conditions present at the tumor site (e.g. when exposed to tumor-associated enzymes or acidic pH) may be used.

In view of the large number of methods that have been reported for attaching a variety of radiodiagnostic compounds, radiotherapeutic compounds, drugs, toxins, and other agents to antibodies one skilled in the art will be able to determine a suitable method for attaching a given agent to an antibody or other polypeptide.

Pharmaceutical Compositions and Administration

The antibody and/or immunoconjugate compositions of this disclosure (i.e., PE linked to an anti-ganglioside antibody), are particularly useful for parenteral administration, such as intravenous administration or administration into a body cavity or lumen of an organ. For example, ovarian malignancies may be treated by intravenous administration or by localized delivery to the tissue surrounding the tumor.

The compositions for administration will commonly comprise a solution of the antibody and/or immunoconjugate dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of fusion protein in these formulations can vary widely, and will be selected primarily based on fluid volumes, viscosities, body weight and the like in accordance with the particular mode of administration selected and the patient's needs.

Thus, a typical pharmaceutical immunotoxin composition of the present invention for intravenous administration would be about 0.1 to 10 mg per patient per day. Dosages from 0.1 up to about 100 mg per patient per day may be used, particularly if the drug is administered to a secluded site and not into the circulatory or lymph system, such as into a body cavity or into a lumen of an organ. Actual methods for preparing administrable compositions will be known or apparent to those skilled in the art and are described in more detail in such publications as REMINGTON'S PHARMACEUTICAL SCIENCE, 19TH ED., Mack Publishing Company, Easton, Pa. (1995).

The compositions of the present invention can be administered for therapeutic treatments. In therapeutic applications, compositions are administered to a patient suffering from a disease, in an amount sufficient to cure or at least partially arrest the disease and its complications. An amount adequate to accomplish this is defined as a "therapeutically effective dose." Amounts effective for this use will depend upon the severity of the disease and the general state of the patient's health. An effective amount of the compound is that which provides either subjective relief of a symptom(s) or an objectively identifiable improvement as noted by the clinician or other qualified observer.

Single or multiple administrations of the compositions are administered depending on the dosage and frequency as required and tolerated by the patient. In any event, the composition should provide a sufficient quantity of the proteins of this invention to effectively treat the patient. Preferably, the dosage is administered once but may be applied periodically until either a therapeutic result is achieved or until side effects warrant discontinuation of therapy. Generally, the dose is sufficient to treat or ameliorate symptoms or signs of disease without producing unacceptable toxicity to the patient.

Controlled release parenteral formulations of the immunoconjugate compositions of the present disclosure can be made as implants, oily injections, or as particulate systems. For a broad overview of protein delivery systems see, Banga, A. J., THERAPEUTIC PEPTIDES AND PROTEINS: FORMULATION, PROCESSING, AND DELIVERY SYSTEMS, Technomic Publishing Company, Inc., Lancaster, Pa., (1995) incorporated herein by reference. Particulate systems include microspheres, microparticles, microcapsules, nanocapsules, nanospheres, and nanoparticles. Microcapsules contain the therapeutic protein as a central core. In microspheres the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly. See, e.g., Kreuter, J., COLLOIDAL DRUG DELIVERY SYSTEMS, J. Kreuter, ed., Marcel Dekker, Inc., New York, N.Y., pp. 219-342 (1994); and Tice & Tabibi, TREATISE ON CONTROLLED DRUG DELIVERY, A. Kydonieus, ed., Marcel Dekker, Inc. New York, N.Y., pp. 315-339 (1992) both of which are incorporated herein by reference.

Polymers can be used for ion-controlled release of immunoconjugate compositions of the present invention. Various degradable and nondegradable polymeric matrices for use in controlled drug delivery are known in the art (Langer, R., Accounts Chem. Res. 26:537-542 (1993)). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston, et al., Pharm. Res. 9:425-434 (1992); and Pec, et al., J. Parent. Sci. Tech. 44(2):58-65 (1990)). Alternatively, hydroxyapatite has been used as a microcarrier for controlled release of proteins (Ijntema, et al., Int. J. Pharm. 112:215-224 (1994)). In yet another aspect, liposomes are used for controlled release as well as drug targeting of the lipid-capsulated drug (Betageri, et al., LIPOSOME DRUG DELIVERY SYSTEMS, Technomic Publishing Co., Inc., Lancaster, Pa. (1993)). Numerous additional systems for controlled delivery of therapeutic proteins are known. See, e.g., U.S. Pat. Nos. 5,055,303, 5,188,837, 4,235,871, 4,501,728, 4,837,028 4,957,735 and 5,019,369, 5,055,303; 5,514,670; 5,413,797; 5,268,164; 5,004,697; 4,902,505; 5,506,206, 5,271,961; 5,254,342 and 5,534,496, each of which is incorporated herein by reference.

Among various uses of the immunotoxins of the present invention are included a variety of disease conditions caused by specific human cells that may be eliminated by the toxic action of the fusion protein. One preferred application for the immunotoxins of the invention is the treatment of malignant cells expressing gangliosides. Exemplary malignant cells include astrocytomas, glioblastomas, and the like.

Diagnostic Kits

In another embodiment, this invention provides for kits for the detection of ganglioside or an immunoreactive fragment thereof, (i.e., collectively, a "ganglioside protein") in a biological sample. A "biological sample" as used herein is a sample of biological tissue or fluid that contains ganglioside. Such samples include, but are not limited to, tissue from biopsy, sputum, amniotic fluid, blood, and blood cells (e.g., white cells). Fluid samples may be of some interest, but are generally not preferred herein since detectable concentrations of ganglioside are rarely found in such a sample. Biological samples also include sections of tissues, such as frozen sections taken for histological purposes. A biological sample is typically obtained from a multicellular eukaryote, preferably a mammal such as rat, mice, cow, dog, guinea pig, or rabbit, and most preferably a primate such as macaques, chimpanzees, or humans.

Kits will typically comprise an anti-ganglioside antibody of the present disclosure. In some embodiments, the anti-ganglioside antibody will be an anti-ganglioside Fv fragment; preferably a scFv fragment.

In addition the kits will typically include instructional materials disclosing means of use of an antibody of the present disclosure (e.g. for detection of glioma cells in a sample). The kits may also include additional components to facilitate the particular application for which the kit is designed. Thus, for example, the kit may additionally contain means of detecting the label (e.g. enzyme substrates for enzymatic labels, filter sets to detect fluorescent labels, appropriate secondary labels such as a sheep anti-mouse-HRP, or the like). The kits may additionally include buffers and other reagents routinely used for the practice of a particular method. Such kits and appropriate contents are well known to those of skill in the art.

In one embodiment of the present disclosure, the diagnostic kit comprises an immunoassay. As described above, although the details of the immunoassays of the present disclosure may vary with the particular format employed, the method of detecting ganglioside in a biological sample generally comprises the steps of contacting the biological sample with an antibody which specifically reacts, under immunologically reactive conditions, to ganglioside. The antibody is allowed to bind to ganglioside under immunologically reactive conditions, and the presence of the bound antibody is detected directly or indirectly.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

EXAMPLE 1

Materials and Methods

Animals, Cell Lines, Xenograft, and Tissues

The β3Gn-T5 knockout mice were recently developed at Duke University Medical Center. P3U1 cells were obtained from the American Type Culture Collection (Manassas, Va.), and we established a D54 glioblastoma cell line at Duke [16]. P3U1 and D54 cells were cultured at 37° C. in a humidified atmosphere of 5% $CO_2$ and 95% air in RPMI 1640 medium including 2 mM L-glutamine (Invitrogen Corp., Carlsbad, Calif.) and 1% of penicillin-streptomycin solution (Invitrogen Corp.) or Zinc Option medium supplemented with 10% heat-inactivated fetal bovine serum (FBS; Sigma, St. Louis, Mo.), respectively. We established and maintained a D54 xenograft at Duke, using human tissue from anonymous donors, which was obtained from the Tissue Bank at the Preston Robert Tisch Brain Tumor Center at Duke.

Antibodies and Gangliosides

Anti-ganglioside antibodies SL-50, DMab-14, and DMab-22 were previously produced at the University of Gothenburg (SL-50) and at Duke University (DMab-14 and -22) [16-18]. Isotype control of mouse $IgG_3$ was purchased from eBioscience, Inc. (San Diego, Calif.). All gangliosides used for immunization or enzyme-linked immunosorbent assay (ELISA) were isolated and characterized at the University of Gothenburg as described previously [19].

Hybridoma Production

The β3Gn-T5 knockout mice were immunized by neck subcutaneous injections of 20 μg of purified 3'-isoLM1 and 3',6'-isoLD1 coupled to *Salmonella minnesota* with Imject™ Freund's Complete Adjuvant (Thermo Scientific Inc., Rockford, Ill.). One week later, secondary i.p. immunization of 20 μg of purified gangliosides was performed. After additional immunization of 20 μg of purified gangliosides, a booster injection was given i.p. 2 days before spleen cells were harvested. The spleen cells were fused with mouse myeloma P3U1 cells by using Sendai virus (hemagglutinating virus of Japan: HVJ) envelope: GenomONE™ $CF_{EX}$ Sendai virus (HVJ) Envelope Cell Fusion Kit (Cosmo Bio USA, Inc., Carlsbad, Calif.) according to the manufacturer's instructions. The hybridomas were grown in RPMI medium including hypoxanthine, aminopterin, and thymidine selection medium supplement (Sigma), 2 mM L-glutamine (Invitrogen Corp.), 10% heat-inactivated FBS (Sigma), 5% BriClone (QED Bioscience Inc., San Diego, Calif.), and 1% of penicillin-streptomycin solution (Invitrogen Corp.). The culture supernatants were screened by ELISA for the binding to 3'-isoLM1 conjugated with bovine serum albumin (BSA). Single cell cloning was performed with ClonaCell™ HY Hybridoma Selection Medium (Medium D; StemCell Technologies Inc., Vancouver, BC, Canada). The IgG subclass was determined by IsoStrip™ Mouse Monoclonal Antibody Isotyping Kit (Roche Diagnostics Corp., Indianapolis, Ind.).

ELISA

For evaluation by ELISA, gangliosides conjugated with BSA were immobilized on 96-well plates at 1 μg/ml for 30 min. After blocking with 1% BSA in PBS, the plates were incubated with primary antibodies at several concentrations, followed by 1:1000 diluted peroxidase-conjugated anti-mouse IgG (GE Healthcare UK Ltd., Buckinghamshire, England). The enzymatic reaction was conducted with a substrate solution containing 3,3',5,5'-tetramethylbenzidine (TMB; Thermo Scientific Inc.). After the reaction was stopped with 2 M $H_2SO_4$, the optical density was measured at 450 nm with a microplate reader (Bio-Rad Laboratories, Inc., Philadelphia, Pa.). These reactions were performed with a volume of 50 μl at room temperature.

SDS-PAGE

For sodium dodecyl sulfate polyacrylamide gel electrophoresis, 2 μg of each protein was electrophoresed under reducing conditions on 4-10% NuPAGE™ gel (Invitrogen). The gel was stained with Bio-Safe™ Coomassie stain (Bio-Rad Laboratories, Inc.).

Flow Cytometry

D54 or D54 xenograft cells, which were collected by 0.6 mM EDTA treatment, were incubated with GMab-1 or isotype control (10 μg/ml) for 1 h at 4° C. Then the cells were incubated with the Oregon green-conjugated anti-mouse antibody (1/200 dilution; Invitrogen Corp.) for 30 min. Flow cytometry was performed with a FACS Calibur™ flow cytometer (Becton Dickinson, Franklin Lakes, N.J.).

Affinity Constant Determination by Surface Plasmon Resonance

To determine the affinity constant ($K_A$), purified GMab-1 was immobilized on the surface of biosensor chips for analysis by using the BIAcore 3000 system (BIAcore, Piscataway, N.J.). Coupling of antigen was achieved by using N-ethyl-N'-(3-dimethylaminopropyl)carbodiimide/N-hydroxysuccinimide according to the instructions of the manufacturer. The running buffer was 10 nM HEPES, 150 mM NaCl, and 3.4 mM EDTA (pH 7.4). The gangliosides conjugated with BSA and control BSA were passed over the biosensor chip and affinity rate constants (association rate constant: $k_{assoc}$ and disassociation rate constant: $k_{diss}$) were determined by nonlinear curve-fitting using the Langmuir one-site binding model of the BIAevaluation software (BIAcore). $K_A$ at equilibrium was calculated as $K_A=k_{assoc}/k_{diss}$.

Immunohistochemical Analysis

All procedures were performed with the Ventana Discovery XT system (Ventana Medical Systems, Inc., Tucson, Ariz.). Briefly, acetone-fixed 5- to 8-μm frozen tissue sections of human glioblastoma tissues were incubated with GMab-1 (10 μg/ml) or isotype control (10 μg/ml) for 30 min. The universal biotin-conjugated secondary antibody was incubated for 20 min followed by the peroxidase-conjugated streptavidin for 16 min. Color was developed by using 3,3'-diaminobenzidine tetrahydrochloride for 8 min, and counterstained by hematoxylin.

EXAMPLE 2

Production of an Anti-3'-isoLM1/3',6'-isoLD1-Specific Antibody

Figure 1B:
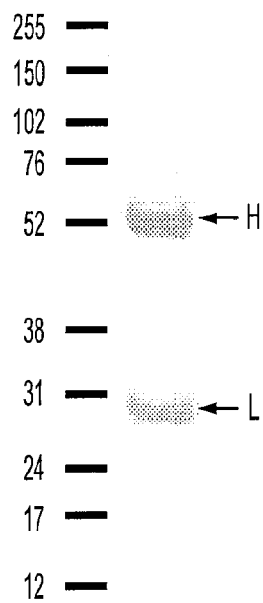
Figure 1C:
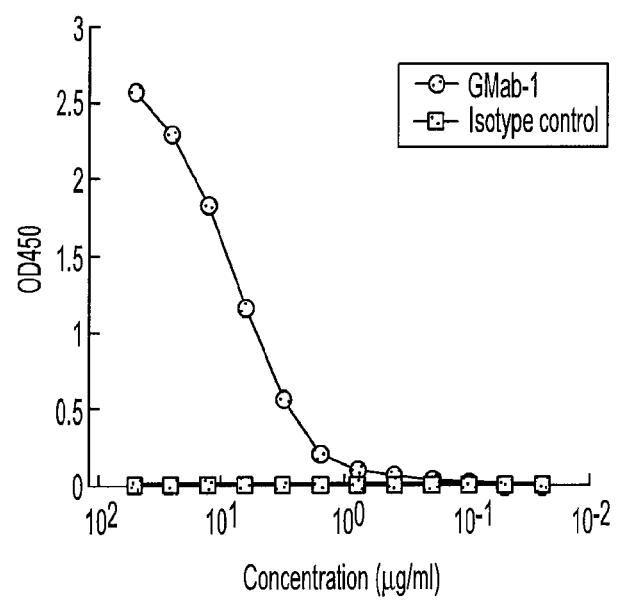
Figure 2A:
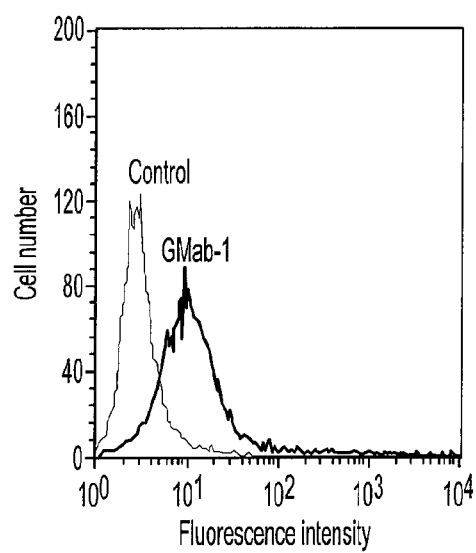
FIG. 2A-2B. GMab-1 recognition of lacto-series ganglioside on the cell surface of glioblastoma cells by flow cytometry. D54 cell line (FIG. 2A) or D54 xenograft cells (FIG. 2B), which were collected by 0.6 mM EDTA treatment, were incubated with GMab-1 or isotype control.
Figure 2B:
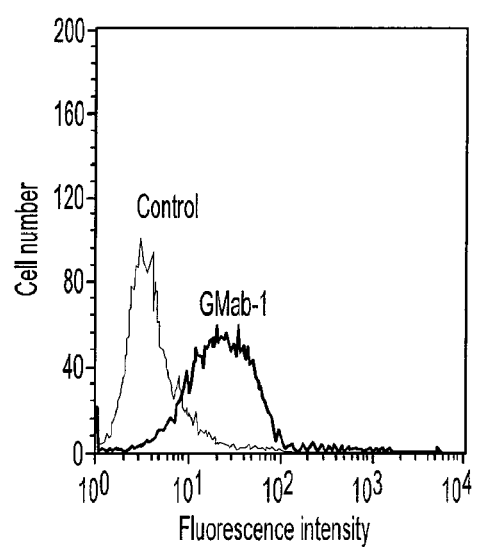

Monoclonal antibodies recognizing lacto-series gangliosides such as 3'-isoLM1 and 3',6'-isoLD1 were previously produced and fully characterized [16, 17]. The 3'-isoLM1 and 3',6'-isoLD1 gangliosides are expressed at high frequency in human glioblastomas and are rarely detected in the normal adult brain. Therefore, 3'-isoLM1 and 3',6'-isoLD1 are ideal molecular targets for immunotherapy against glioblastomas using specific mAbs. However, those established mAbs have relatively low-affinity against 3'-isoLM1 and 3',6'-isoLD1 because they are of the IgM subclass. In several studies, anti-ganglio-series ganglioside mAbs with high affinity have been developed by immunizing GalNAcT$^{-/-}$ mice with ganglio-series gangliosides [2, 6, 13, 14]. Similarly, in this study, we immunized β3Gn-T5 knockout mice with purified 3'-isoLM1 and 3',6'-isoLD1 coupled to *Salmonella minnesota* to generate high-affinity anti-lacto-series ganglioside mAbs (FIG. 1A). Because the hybridomas that we previously produced from β3Gn-T5 knockout mice using the conventional polyethylene glycol fusion method had low viability (data not shown), for this study, we selected a low-toxicity, high-efficiency fusion method using a Sendai virus envelope [20]. After single cell cloning, one of the clones, GMab-1 (IgG$_3$ subclass) was established (FIG. 1B). As shown in FIG. 1C, GMab-1 reacted with 3'-isoLM1 in a dose-dependent manner in ELISA. Furthermore, both D54 cells and D54 xenograft cells, which express lacto-series gangliosides were recognized by GMab-1 as demonstrated by flow cytometry (FIG. 2A-2B). To determine the association and dissociation rate constants ($k_{assoc}$ and $k_{diss}$) and to calculate the affinity constants ($K_A$), we next performed a kinetic analysis of the interaction of GMab-1 with 3'-isoLM1 by surface plasmon resonance (BIAcore). Determination of the association and dissociation rates from the sensorgrams revealed a $k_{assoc}$ of 5.07×10$^4$ (mol/L-s)$^{-1}$ and a $k_{diss}$ of 2.74×10$^{-4}$ s$^{-1}$. The $K_A$ at binding equilibrium, calculated as $K_A=k_{assoc}/k_{diss}$, was 1.85×10$^8$ (mol/L)$^{-1}$, indicating that GMab-1 has high affinity against 3'-isoLM1.

EXAMPLE 3

Specificity of GMab-1 Against Gangliosides

Figure 3A:
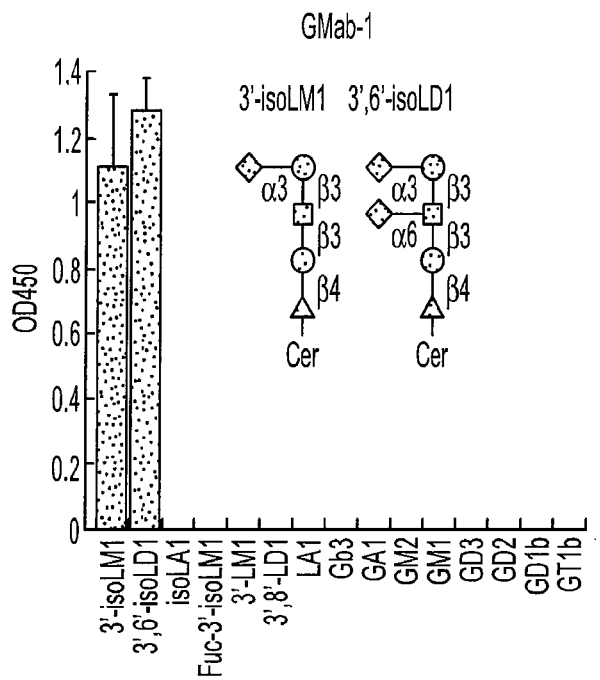
FIG. 3A-3D. Epitope determination of GMab-1 in ELISA. Fifteen gangliosides conjugated with BSA were immobilized. After blocking, the plates were incubated with GMab-1 (FIG. 3A), DMab-14 (FIG. 3B), SL-50 (FIG. 3C), and DMab-22 (FIG. 3D) at a concentration of 10 μg/ml.
Figure 3B:
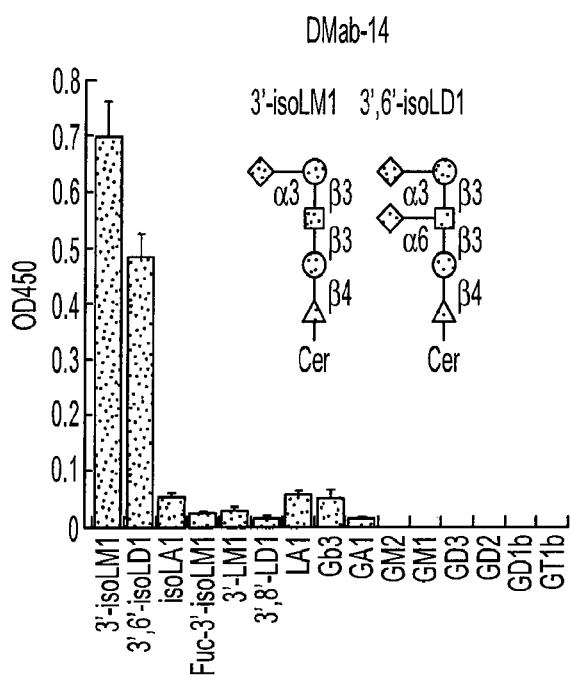
Figure 3C:
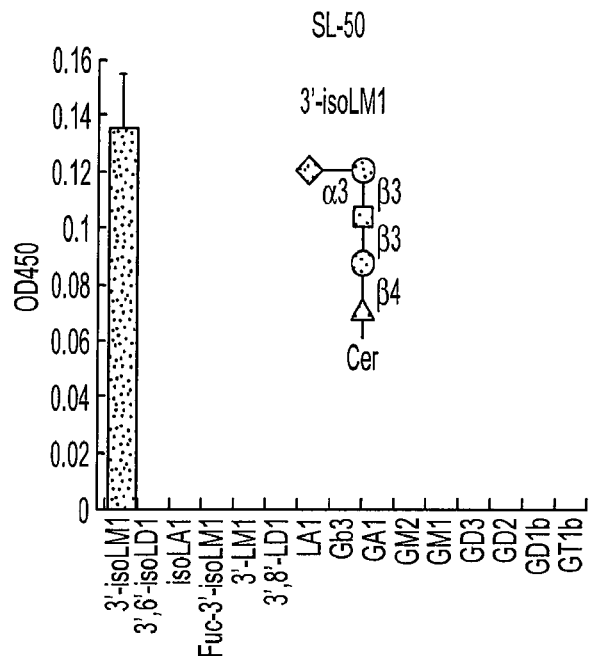
Figure 3D:
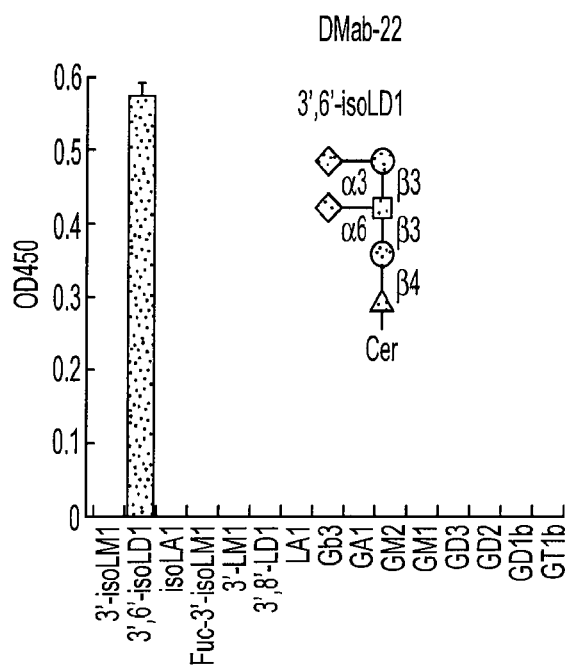

To determine the epitope of GMab-1, we performed ELISA using 15 different gangliosides, including lacto-series (3'-isoLM1, 3',6'-isoLD1, isoLA1, and Fuc-3'-isoLM1), neolacto-series (3'-LM1 and 3',8'-LD1), globo-series (Gb3), asialo-series (GA1), a-series (GM2 and GM1), and b-series (GD3, GD2, GD1b, and GT1b) (A-3D. 3). As previously reported [16, 17], SL-50 reacted with 3'-isoLM1 and not with 3',6'-isoLD1 (FIG. 3C), whereas DMab-22 reacted with 3',6'-isoLD1 and not with 3'-isoLM1 (FIG. 3D). We have observed no cross-reaction with the other gangliosides using SL-50 and DMab-22. DMab-14 reacted with both 3'-isoLM1 and 3',6'-isoLD1; however, there is slight reactivity with the other gangliosides (FIG. 3B). On the other hand, we did observe activity that distinguished GMab-1 from SL-50, DMab-22, and DMab-14. GMab-1 recognized both 3'-isoLM1 and 3',6'-isoLD1, and the reactivity with 3',6'-isoLD1 was stronger than with 3'-isoLM1 (FIG. 3A). Although DMab-14 reacted with both 3'-isoLM1 and 3',6'-isoLD1, the reactivity with 3'-isoLM1 was stronger than with 3',6'-isoLD1 (FIG. 3B), which indicates that the epitope of GMab-1 is slightly different from that of DMab-14. Furthermore, there is no cross-reaction with the other gangliosides using GMab-1 (FIG. 3A). These results indicate that GMab-1 defines the epitope NeuAcα2-3Galβ1-3GlcNAc, the terminal sequence in 3'-isoLM1 and 3',6'-isoLD1.

EXAMPLE 4

Immunohistochemical Analysis by GMab-1 Against Glioblastoma Tissues

Figure 4B:
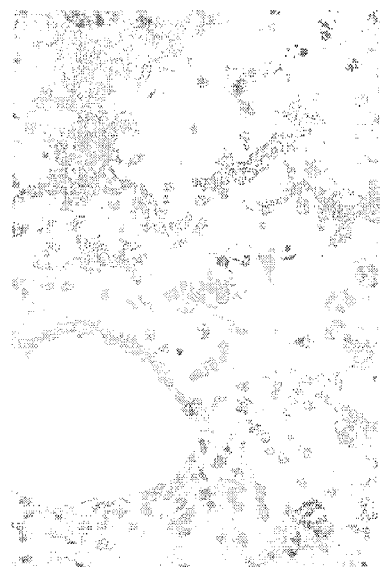
FIG. 4A-4D. Immunohistochemical analysis by GMab-1 against glioblastoma tissues. Glioblastoma tissues were stained by GMab-1 (FIG. 4A, FIG. 4C) or isotype control (FIG. 4B, FIG. 4D). Magnification: ×200.
Figure 4D:
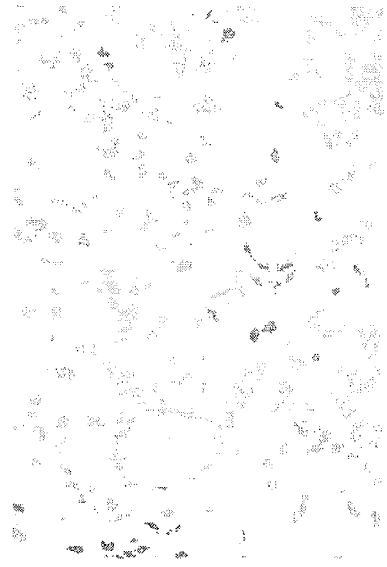
Figure 4A:
Figure 4C:
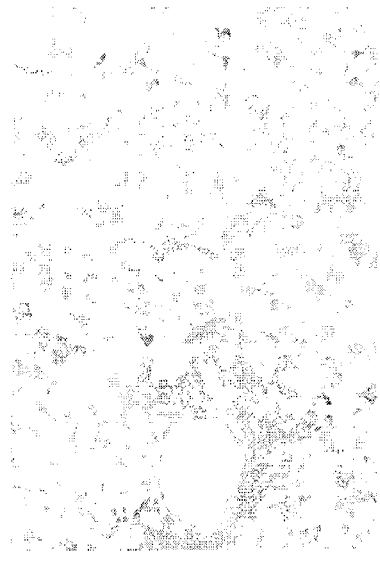

Since lacto-series gangliosides such as 3'-isoLM1 and 3',6'-isoLD1 are known to be expressed in glioblastoma tissues [18], immunohistochemistry was performed using 33 glioblastoma frozen tissue specimens. GMab-1 immunoreactivity was detected in 26 of 33 (78.8%) glioblastomas. Representative staining by GMab-1 in glioblastoma samples is shown in FIG. 4A-4D. Immunostaining by GMab-1 demonstrated predominantly both cell-surface patterns (FIG. 4A) and cell-surface/cytoplasmic patterns (FIG. 4C) in glioblastoma cells. Proliferating endothelial cells were negative for GMab-1 (FIG. 4A). The concentration-matched isotype control of mouse IgG$_3$ did not stain any tumor cells (FIGS. 4B and 4D). These results further suggest that GMab-1 specifically reacted with lacto-series gangliosides in glioblastoma tissues.

In conclusion, we immunized β3Gn-T5 knockout mice with 3'-isoLM1 and 3',6'-isoLD1. GMab-1 (SEQ ID NO:17 and 20), of the IgG$_3$ subclass, specifically recognized both 3'-isoLM1 and 3',6'-isoLD1 and showed high binding activity. GMab-1 was also reactive against glioblastomas in immunohistochemical analyses, suggesting that GMab-1 should be useful in antibody-based therapy of glioblastomas.

EXAMPLE 5

Additional Antibodies

We isolated an additional antibody produced by a hybridoma as described in Example 2 above. Antibody GMab-2 (SEQ ID NO: 18 and 21) is of the IgG$_{2b}$ subclass and specifically binds to both 3'-isoLM1 and 3',6'-isoLD1.

Thus its binding specificity is similar to GMab-1. Binding specificities were tested by enzyme linked immunosorbent assays (ELISA). Control antibodies were the SL-50 IgM antibody which is specific for 3'-isoLM1 and DMab-22, which is specific for 3',6'-isoLD1.

GMab-2 did not bind to any of isoLA1, Fuc-3'-isoLM1, 3'-LM1, 3',8'-LD1, LA1, Gb3, GM1, GD1b, GT1b, GA1, GD3, GM2, or GD2, defining its epitopic specificity.

EXAMPLE 6

Affinity Maturation

We constructed a recombinant single chain variable fragment (scFv) from previously isolated, hybridoma DMab14 (SEQ ID NO: 19 and 22). The IgM antibodies made by DMAB14 recognize both 3' iso-LM1 and 3'6' iso-LD1 gangliosides, which are tumor associated antigens. Wikstand C J et al., *J. Neuropathol. Exp. Neurol.* 1991, vol. 50:756-769. We fused the scFv with *Pseudomonas* exotoxin A (PE38) at the carboxy terminus of the scFv. We investigated the binding affinity and specificity of the resulting recombinant immunotoxin for gangliosides 3' iso-LM1 and 3'6' iso-LD1 on D54 MG cultured cells. These cells were previously shown to highly express these gangliosides on their cell surfaces. The parental version of DMab14-scFv showed a binding affinity of $K_d$=7.5×10-e7M to D54 MG but did not demonstrate any cytotoxicity to cell line D54 MG. After five rounds of affinity maturation by phage display, a new generation of DMab14-scFv was generated, which was dubbed DMab14-86184-PEKDEL. (For review of display technologies including affinity maturation by phage display, see Sergeeva et al., Adv. Drug Deliv. Rev. 2006, vol. 58: 1622-1654.) DMab14-86184-PEKDEL contains a combination of mutations in the VHCDR2 and in the VLCDR1. FIG. 5. The binding affinity of DMab14-86184-PEKDEL to D54 MG cells was determined to be $K_d$=7.16×10-e8M. DMab14-86184-PEKDEL demonstrated cytotoxicity against cell line D54 MG. In protein synthesis inhibition assays and cell proliferation assays DMab14-86184-PEKDEL displayed IC50=80 ng/ml and $IC_{50}$<1000 ng/ml, respectively. Moreover, when tested against the H336 cell line, DMab14-86184-PEKDEL demonstrated a $K_d$=2.9×10-e7M and an IC50=10 ng/ml. In vivo studies are underway. Preliminary results indicate that DMab14-86184-PEKDEL has significant potential for treating brain tumors. Elimination of cells expressing 3' iso-LM1 and 3'6'-isoLD1 should result in significant survival increases in brain tumor patients.

Materials and Methods:

Cloning of variable heavy ($V_H$) and variable light ($V_L$) domains of DMAb14. We isolated total cellular mRNA from $10^6$ DMAb14-hybridoma cells by using the RNeasy Kit (Invitrogen, Carlsbad, Calif.). Primary $V_H$ and $V_L$ genes of the parental DMAb14 clone were amplified by RACE-PCR (Rapid Amplification of cDNA Ends-PCR) using a SMART 5'-RACE cDNA amplification kit (Clontech, Palo Alto, Calif.). The 3' primers were mouse heavy-chain (HC) and light-chain (LC) constant region sequences of the immuno-globulin ($V_H$: 5'-GGC CAG TGG ATA GTC AGA TGG GGG TGT CGT TTT GGC-3' (SEQ ID NO: 23) and $V_L$: 5'-GGA TAC AGT TGG TGC AGC ATC-3')(SEQ ID NO:24). The primary $V_H$ and $V_L$ cDNA genes obtained from 5'-RACE were then used as templates to specifically amplify the $V_H$ and $V_L$ fragments respectively by using specific primers introduced at restriction enzyme sites and a (Gly$_4$Ser)$_5$ (SEQ ID NO: 71) linker sequence for scFv assembly and subsequent subcloning. The oligomers used for these reactions were as follows: DMAb14-H-F (NcoI), 5'-GCC GCC ACCA TG Gag GTC CAA CTG CAG-3'(SEQ ID NO: 25); DMAb14-H-R (linker), 5'-AGA TCC GCC ACC ACC GGA TCC CCC TCC GCC TGA GGA GAC GGT GAC-3'(SEQ ID NO: 26); DMAb14-L-F (linker), 5'-GGT GGT GGC GGA TCT GGA GGT GGC GGC AGC GGT AAC ATT GTG CTG-3'(SEQ ID NO: 27); and DMAb14-L-R (EcoRI), 5'-GCAGCC GAATT CAT TTT TAT TTC CAG CTT G-3'(SEQ ID NO: 28). We aligned and verified the outcome-specific $V_H$ and $V_L$ sequences according to the Kabat alignment scheme. We constructed DMAb14-scFv using PCR splicing technology. In brief, we mixed Advantage™ 2 DNA polymerase (Clontech) with 50 ng each of $V_H$ and $V_L$ PCR fragments at a 1:1 ratio in the presence of bovine serum albumin (BSA) in a 50-4, volume. The PCR mix was cycled by using the following profile: 1 cycle at 96° C. for 5 minutes; followed by 5 cycles each at 94° C. for 1 minute, 55° C. for 1 minute, and 72° C. for 1 minute and 30 seconds; and a final cycle at 72° C. for 7 minutes. We paused the program at 4° C. for 2 minutes to add premixed oligomers, namely, the forward and reverse primers that had been used to generate the $V_H$ and $V_L$ fragments. The reaction was then continued as follows: 1 cycle at 96° C. for 5 minutes; followed by 25 cycles each at 94° C. for 1 minute, 55° C. for 1 minute, and 72° C. for 1 minute and 30 seconds; and finally terminated at 72° C. for 7 minutes. A 750-bp PCR product generated from this reaction was then purified by using QiaQuick™ Spin columns (Qiagen, Valencia, Calif.) and double digestion with NcoI and EcoRI and subcloned into a T7 bacterial expression vector pET25b(+) (Novagen, Madison, Wis.). We verified the parental DMAb14-scFv sequence by the dideoxy chain-termination method.

Preparation of Recombinant Immunotoxins.

We generated the DMAb14-scFv IT by PCR using parental DMAb14-scFv plasmid as a template and primers introduced at the NdeI and HindIII restriction enzyme sites. After NdeI and HindIII digestion, we inserted the scFv fragment into pRB199 bacterial expression vector that had been engineered with the sequence for domains II and III of *Pseudomonas* exotoxin A (PE38 KDEL) according to a previously described protocol (15). The parental DMAb14-scFv IT was expressed under control of the T7 promoter in *E. coli* BL21 (λ DE3) (Stratagene, La Jolla, Calif.). All recombinant proteins remained in the inclusion bodies. We then reduced, refolded, and further purified the IT proteins as monomers (67 kDa) by using ion-exchange and size-exclusion chromatography to greater than 90% purity.

Construction of DMAb14-scFv Phagemid.

We constructed the parental DMAb14-scFv phagemid by PCR amplification from parental DMAb14-scFv-pRB199 PE38 KDEL. We used the following oligomers, which were introduced at the NcoI and NotI restriction enzyme sites: DMAb14-scFv-F (NcoI), 5'-GCCGCCA CCATG GAG GTC CAA CTG CAG-3'(SEQ ID NO: 29), and DMAb14-scFv-R(NotI), 5'-ATG ATG TGC GGC CGC TTT TAT T TC CAG CTT G-3'(SEQ ID NO: 30). The PCR product was digested with NcoI and NotI and inserted into the phagemid vector pHEN2. We used the resulting parental phagemid DMAb14-scFv-pHEN2 as a template for further construction of mutant phage libraries.

Construction of $V_H$ Mutant Library.

Figure 7B:
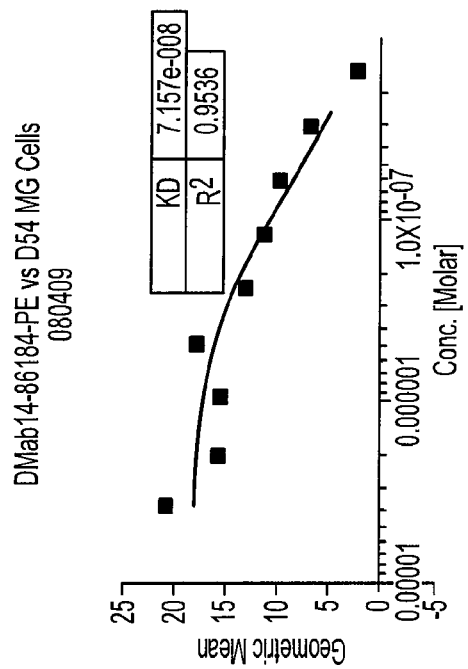
FIG. 7A-7B. DMab14-86184-scFv-PEKDEL protein binding affinity was measured on D54MG cells by flow cytometry.
Figure 7A:
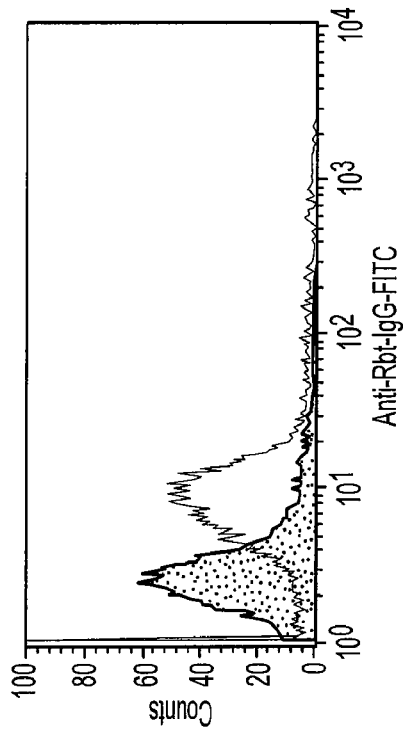

The $V_H$CDR2 of DMAb14 consisted of 18 amino acids. We designed DNA oligomers to generate 3 libraries, each randomizing 9 nucleotides (3 consecutive amino acids). We used degenerate oligomers with the sequence NNS for randomizing (N randomizing with all 4 nucleotides, and S introducing only C or G) (16). Parental DMAb14 phagemid was used as a template to introduce 3 amino acid randomizations in the CDR2 heavy chain in 3 separate 2-step PCRs (FIG. 7A, 7B). We used the following oligonucleotides: (a) DMAb14-VHCDR2a-R, 5'-GTT AGT ACG ACC GTT SNN SNN SNN AAT CTC TCC AAT CC-3'(SEQ ID NO: 31); (b)

DMAb14-VHCDR2b-R, 5'-AAT ATA GTT AGT ACG SNN SNN SNN AGG ATT AAT CTC TCC-3'(SEQ ID NO: 32); (c) DMAb14-VHCDR2c-R, 5'-TAC AGT CAG TGT GGC SNN SNN SNN GAA CTT CTC-3'(SEQ ID NO: 33); (d) DMAb14-scFv-F (NcoI), 5'-GCCGCCA CCATG GAG GTC CAA CTG CAG-3'(SEQ ID NO: 34); and (e) DMAb14-scFv-R (NotI), 5'-ATG ATG TGC GGC CGC TTT TAT T TC CAG CTT G-3'(SEQ ID NO: 35). In the first PCR, we used 50 pg of the phagemid DMAb14-scFv-pHEN2 as a template in 3 separate reactions involving 20 pmol of DNA oligomer DMAb14-scFv-F (NcoI), along with 20 pmol of DNA oligomer DMAb14-VHCDR2a-R, DMAb14-VHCDR2b-R, or DMAb14-VHCDR2c-R (FIG. 7A). The template and oligonucleotides were mixed with Advantage 2 PCR Kit (Clontech) in a 50-μL volume and then cycled using the following profile: 1 cycle at 95° C. for 5 minutes, followed by 30 cycles each at 94° C. for 1 minute, 55° C. for 1 minute, and 72° C. for 1 minute. This reaction generated 280-bp products that contained mutations. The products were purified by using Qiagen Quick Spin columns (Qiagen, Inc.) and then quantified by visualization on a 1% agarose gel. We used the purified products generated in the first PCR as primers in a second PCR. In the second reaction, we used approximately 2 pmol each of the 3 products containing mutations obtained from the first reaction and the NcoI restriction enzyme site, along with 20 pmol of the DNA oligomer DMAb14-scFv-R (NotI) and 50 pg of the parental phagemid DMAb14-scFv-pHEN2 as a template to generate the whole length of the scFv-$V_H$ mutation pool (FIG. 7B). The PCRs were set and cycled by using the profile described above. Each reaction generated 750-bp insert libraries. The PCR product was digested with NcoI and NotI and purified by using Qiaquick columns (Qiagen, Inc.). The purified PCR product (80 ng) was ligated with 150 ng of the phage display vector pHEN2 (predigested with NcoI and NotI) and desalted. We used 40 ng of ligated products to transform E. coli TG1 (Stratagene, La Jolla, Calif.) by electroporation. We performed 3 transformations to create a library containing 6×10⁴ clones. We then rescued the phage libraries from the transformed bacteria. Cells from each transformation were grown in 10 mL of 2×YT (Bacto Yeast Extract and Bacto Tryptone) containing 2% glucose at 37° C. with shaking at 250 rpm. After 1 hour, we added ampicillin (100 μg/mL, final concentration) and 1×10$^{11}$ plaque-forming units (pfu)/mL of VCSM13 Interference-Resistant Helper Phage (Stratagene, Agilent Technologies, Palo Alto, Calif.). The cultures were grown for 1 hour, pelleted, resuspended in 10 mL of 2×YT supplemented with ampicillin (100 μg/mL) and kanamycin (50 μg/mL), and grown for 16 hours at 30° C. with shaking at 250 rpm. The bacteria were pelleted by centrifugation in a Sorvall SS34 rotor at 8000 rpm for 20 minutes. The phage-containing supernatants were filtered through a 0.45-μm syringe filter unit. The phages were precipitated by adding 2 mL of PEG/NaCl (20% PEG8000 in 2.5M NaCl [w/v]) and incubated on ice for 30 minutes. The precipitated phages were pelleted by centrifugation in a Sorvall SS34 rotor at 10,000 rpm for 20 minutes and resuspended in 1 mL of NTE [100 mM NaCl, 10 mM Tris (pH 7.5), and 1 mM EDTA]. The rescued phage libraries were titered and stored at 4° C.

Screening of $V_H$ Mutant Library by Phage ELISA.

We cultured and plated a diluted $V_H$CDR2 mutant phage library. Recombinant phage-containing supernatants were rescued from individual clones and screened by antigen-based phage ELISA. We picked single colonies from the diluted library plates and inoculated them into 1 mL of 2×YT medium supplemented with 2% glucose and 100 μg/mL of ampicillin. The colonies were cultured overnight at 37° C. with shaking. To one cultured colony preparation, we added 450 μL of 2×YT supplemented with 2% glucose and 100 μg/mL of ampicillin contained 2.5×10⁸ pfu of VCSM13 Interference-Resistant Helper Phage (Stratagene) in 1.2-mL Cluster Tubes (Corning Incorporated, Corning, N.Y.). To another preparation, we added 50 μL of the overnight culture and then incubated the colony at 37° C. for 2 hours with shaking at 250 rpm. The cells were pelleted and resuspended in 500 μL 2×YT containing 100 μg/mL ampicillin and 50 μg/mL kanamycin without glucose and then grown for 16 hours at 30° C. The cells were again pelleted by centrifugation at 2800 rpm at 4° C., and the phage-containing supernatants were saved.

Purified gangliosides 3'-isoLM1 and 3'6'-isoLD1 conjugated with BSA (purified from the D54 MG xenograft, Sahlgrenska University Hospital, Gothenburg, Sweden) in PBS were immobilized overnight in 96-well plates (Nunc, Thermo Fisher Scientific, NY) containing 50 ng/well at room temperature. We blocked the plates with 1% BSA/PBS at 37° C. for 30 minutes and then washed them 3 times with 0.05% Tween™ 20 polyethylene glycol sorbitan monolaurate (non-ionic detergent) in PBS by using a Bio-Rad™ Auto-Washer (Bio-Rad 1575 Immuno Wash Microplate Washer). We then added 100 μL/well of phage-containing supernatant for a 1-hour incubation at 37° C. and washed the plates 3 times as above. For phage ELISA, we added 100 μL/well of anti-M13 antibody-horseradish peroxidase (HRP) conjugate (Pharmacia Biotech, Sweden) in blocking buffer, diluted according to the manufacturer's instructions, to detect phage binders. For monoclonal IgM antibody, we added 100 μL/well of anti-mouse IgM HRP conjugate (μ-Chain Specific; Sigma, St. Louis, Mo.) in blocking buffer (1:10,000 dilution). After 30 minutes of incubation at 37° C., we washed the plates and used 100 μL/well of 3,3',5,5'-tetramethyl benzidine (1-Step Ultra TMB-ELISA, Pierce, Rockford, Ill.) solution as a substrate for detection. After a blue color developed, we added 50 μL TMB Stop Solution (Pierce) to stop further color development. We measured absorption at 450 nm. Clones reacting to gangliosides were referred to as positives.

Construction of $V_L$ Mutant Library.

The $V_L$CDR1 of DMAb14 consists of 15 amino acids. We used parental DMAb14 phagemid DNA as a template in 4 separate 2-step PCRs that introduced randomizations in the hot spot located in the light-chain CDR1 (FIG. 7A, 7C). We used the following oligonucleotides: (a) DMAb14-VLCDR1a-F, 5'-ACC ATA TCC TGC NNS NNS NNS GAA AGT GTT GAG AGT TAT GGC-3'(SEQ ID NO: 36); (b) DMAb14-VLCDR1b-F, 5'-ACC ATA TCC TGC AGA NNS NNS NNS AGT GTT GAG AGT TAT GGC-3'(SEQ ID NO: 37); (c) DMAb14-VLCDR1c-F, 5'-ACC ATA TCC TGC AGA GCC NNS NNS NNS GTT GAG AGT TAT GGC-3' (SEQ ID NO: 38); (d) DMAb14-VLCDR1d-F, 5'-GCC AGT GAAAGT GTT NNS NNS NNS GGC AAT AAT TTT ATG CAC-3'(SEQ ID NO: 39); (e) DMAb14-scFv-F (NcoI), 5'-GCCGCCA CCATG GAG GTC CAA CTG CAG-3'(SEQ ID NO: 40; and (f) DMAb14-scFv-R (NotI), 5'-ATG ATG TGC GGC CGC TTT TAT T TC CAG CTT G-3'(SEQ ID NO: 41). In the first reaction, we mixed 50 pg of the DMAb14-scFv phagemid DNA with 20 pmol of each pair of DNA oligomers in a 50-μL volume as follows: (a)+(f), (b)+(f), (c)+(f), and (d)+(f). The mixture was cycled by using the same profile used to generate the heavy-chain CDR2 mutant library. The reactions generated 260-bp products exhibiting randomization of the hot spot in the light-chain CDR1. After purification and quantification, 2 pmol of the 260-bp fragments generated in the first PCR, was subjected to a second PCR, along with 20 pmol of DNA oligomer (e) and 50 pg of parental DMAb14-scFv phagemid DNA as a template (FIG. 7C). We carried out the PCR (volume, 50 μL) by using an Advantage™ 2 PCR Kit (Clontech) and following the above-mentioned profile. The reactions generated a 750-bp library, which showed randomization of the hot spot in $V_L$CDR1. The PCR products were then digested with the restriction enzymes NcoI and NotI, purified, and ligated with the pHEN2 phage vector as described for the heavy-chain CDR2 mutant libraries. We desalted the ligation and used one-tenth (40 ng) of the reaction to transform *E. coli* TG1. We rescued the $V_L$CDR1 mutant phage library containing $5 \times 10^4$ clones as described in the heavy-chain CDR2 construction.

Selection of $V_L$CDR1 Library by Phage ELISA.

We cultured and plated a diluted $V_L$CDR1 phage library. The technical procedures used were the same as those described in the $V_H$CDR2 libraries selection.

Construction of $V_H$CDR2 and $V_L$CDR1 Combination Libraries.

We used the heavy-chain CDR2 mutant as a template to generate the $V_H$ fragment. For this purpose, we used the primers DMAb14-H-F (NdeI), 5'-G GCG CAT ATG CAT GTC CAA CTG CAG-3' (SEQ ID NO: 42) and DMAb14-H-R (linker), and 5'-AGA TCC GCC ACC ACC GGA TCC CCC TCC GCC TGA GGA GAC GGT GAC-3' (SEQ ID NO: 43) in a 50-μL volume and an Advantage 2 PCR Kit (Clontech) and obtained a 420-bp product. We used the light-chain CDR1 mutant as a template to generate the $V_L$ fragment. We used the primers DMAb14-L-F (linker), 5'-GGT GGT GGC GGA TCT GGA GGT GGC GGC AGC GGT AAC ATT GTG CTG-3'(SEQ ID NO: 44) and DMAb14-L-R (HindIII), and 5'-C AAG CTG GAA ATA AAA A AA GCT TGG CAG C-3'(SEQ ID NO: 45) in a 50-volume and an Advantage 2 PCR Kit (Clontech) to generate a 335-bp PCR product. mutant $V_H$ and mutant $V_L$ DNA fragments were overlapped by a 15-amino acid linker sequence and connected by using the splicing PCR technique described above, except that the oligomers used in this reaction were DMAb14-H-F (NdeI) and DMAb14-L-R (HindIII), which are listed above in this section. This reaction generated 750-bp products that contained mutations in both the $V_H$ and $V_L$ regions. The products were purified by using Qiagen Quick Spin columns (Qiagen, Inc.), digested with NdeI and HindIII, and cloned into a T7 expression vector pRB199 in which scFv was fused to a truncated version of *Pseudomonas* exotoxin A (PE38 KDEL). Their sequence was then verified.

Analysis of Selected Clone by DNA Sequencing.

Sequencing was performed by the Duke University DNA Sequencing Facility on an Applied Biosystems Dye Terminator Cycle Sequencing system (Life Technologies, Corp., Carlsbad, Calif.) by using AmpliTaq DNA Polymerase and ABI 3730 PRISM DNA Sequencing instruments. Sequencing analysis was performed using the NCBI nucleotide BLAST program.

Cell-Binding Assay and Constant $K_d$ by FACS.

We used a modification of the method reported previously (17) to detect scFv immunotoxin binding to ganglioside-expressing cells. To prevent internalization of the immunotoxin during the assays, we kept all reagents and the buffer on ice. In brief, cells to be tested for scFv immunotoxin binding were harvested by trypsinization, rinsed with 1% FBS in PBS, and portioned to assay tubes (approximately $10^6$ cells per sample). The scFv immunotoxins were serial-diluted in 100 μL of 1% FBS-PBS, with an initial amount of 25.6 μg. The cells were incubated with 100 μL of various dilutions of the purified scFv immunotoxin or anti-Tac(Fv)-PE38-KDEL, a negative control that does not bind to gangliosides, for 1 hour on ice. We then washed the cells twice in 1% FBS-PBS and incubated them with rabbit anti-*Pseudomonas* exotoxin A antibody (Sigma) for 30 minutes on ice. After the cells were washed twice, we reacted them with goat anti-rabbit IgG-FITC conjugate (Sigma) for 30 minutes on ice. The stained cells were again washed twice and then subjected to flow cytometry. We used an identical protocol for binding of the scFv immunotoxin in this study. All reagents were determined to be at saturation point, and binding reached equilibrium for the described conditions in all antibody-binding experiments. We determined equilibrium constants by using the Graph Pad Prism Software (version 4.0) for 1-site binding and nonlinear regression analysis.

Determination of Affinity Constants ($K_d$) by Scatchard Analysis.

We performed affinity measurements by using Iodogen-labeled scFv immunotoxin binding to cells positive and negative for ganglioside expression. We seeded the cells in a 24-well plate, cultured them until confluence, fixed them in 0.25% gluteraldehyde for 5 minutes at room temperature, washed them 3 times with incubation buffer (115 mM $PO_4$ [$KH_2PO_4+K_2HPO_4$] buffer with 0.05% BSA and 0.05% gelatin), and froze them at $-80°$ C. until use. [$^{125}$I]-labeled sample scFv and negative control scFv immunotoxin were serial diluted starting from 8 μg/mL to 4 ng/mL, followed by the addition of various dilutions of $I^{125}$-scFv immunotoxins to corresponding triplicate wells and incubation of the cell plates overnight at 4° C. The next day, we removed the free radioactive antibody and washed the cell plates 4 times with the incubation buffer. We then added 500 μL/well of 2N sodium hydroxide and incubated the cell plates overnight at 37° C. The cells were completely suspended and transferred (including cell debris) into 2-mL screw-capped tubes, which were placed in a gamma counter in order, and the cells were counted. The data obtained were analyzed by normalization based on standard curve and equilibrium constants, and a Scatchard plot was determined with Prism software (version 4.0) for nonlinear regression analysis.

Cytotoxicity Assays.

We measured cytotoxicity using both protein synthesis inhibition and cell death assays. In both assays, we plated cells in 96-well plates (Nunc) at a concentration of $1 \times 10^4$ cells/200 μL/well. We serially diluted immunotoxins in PBS supplemented with 0.2% BSA starting from 10 ng/μL and added 20 μL of each dilution to the corresponding wells, resulting in a maximum immunotoxin concentration of 1000 ng/mL. We incubated the plates for 20 hours at 37° C.

We measured protein synthesis on the basis of [$^3$H] leucine incorporation. We pulsed the cells with 1 μCi/well of [$^3$H] leucine in 20 μL of PBS supplemented with 0.2% BSA for 2.5 h at 37° C. We captured radiolabeled cells on a FilterMate micro-harvester (PerkinElmer Life and Analytical Sciences, Boston, Mass.) and counted them with a Betaplate scintillation counter (Amersham Biosciences, GE Healthcare Bio-Sciences Corp., Piscataway, N.J.). Triplicate sample values were averaged, and the inhibition of protein synthesis was determined by calculating the percentage of incorporation compared with control wells without added toxin. The activity of the molecule was defined as the $IC_{50}$.

We assessed cell death by WST-8 conversion using Cell Counting Kit-8 according to recommendations from the supplier (Dojindo Molecular Technologies, Gaithersburg, Md.). We seeded the cells onto a 96-well plate (Costar, Corning Incorporated) at a concentration of $2 \times 10^4$ cells/100 μL/well. We serially diluted the immunotoxins in PBS supplemented with 0.2% BSA starting from 10 ng/μL and added 10 μL of each dilution to the corresponding wells. The cells were then incubated at 37° C. for 20 h. We added 10 μL of WST-8 (5 mM WST-8, 0.2 mM 1-methoxy-5-methylphenazinium methylsulfate, and 150 mM NaCl) to each well, and continued the incubation at 37° C. We measured the absorbance of the sample at 450 nm every 20 minutes until the highest value for the negative control was obtained. Cytotoxicity was expressed as 50% inhibition of cell viability. We performed all experiments in triplicate. Statistical analyses were performed with Prism software (version 4.0) for Windows (GraphPad software, San Diego Calif.). Each immunotoxin was assayed at least twice, and critical immunotoxins were assayed more frequently.

DMAb14-scFv-Mut Epitope Mapping.

DMAb14-scFv immunotoxins that specifically bind to gangliosides 3'-isoLM1 and 3'6'-isoLD1 were assayed by ELISA. We coated each purified ganglioside (500 pM) in PBS on a 96-well plate (Nunc™), which was blocked with 1% BSA/PBS at 37° C. for 1 h. We applied 500 ng primary antibodies in triplicate and incubated the plate at 37° C. for 30 minutes. We used D2C7 immunotoxin as a scFv structural negative control, SL50 IgM and DMAb22 IgM as positive controls for 3'-isoLM1 and 3'6'-isoLD1, respectively, and MOPC as an IgM negative control. We washed the plate 3 times with 0.05% BSA and 0.05% Tween in PBS. After adding rabbit anti-PE (Sigma; dilution 1:30,000) to the scFv immunotoxins for 30 minutes and washing the plate, we applied anti-rabbit IgG-HRP (Sigma, dilution 1:1,500) and anti-mouse IgM-HRP (Sigma, dilution 1:1,500) to the scFv immunotoxins and IgMs, respectively. The plate was incubated at 37° C. for 30 minutes and washed 3 times with a washing buffer. We then added 100 μL of 1-Step™ Ultra-TMB ELISA substrate solution (Thermal Scientific, Odessa, Tex.) substrate, and the reaction color turned blue within 3-5 minutes; we immediately applied stop solution to terminate the reaction and change the color to yellow. The ELISA plate was read at an absorbance of 450 nm.

Internalization assay. We directly labeled DMAb14-scFv immunotoxins with Alexa Fluor™-488 dye and incubated 50 nM Alexa Fluor™-488 dye-labeled DMAb14-scFv immunotoxin with $3 \times 10^5$ H336 cells or Xeno-2224 cells on ice for 1 hour. After washing the cells twice with ice-cold PBS, we resuspended the cells in zinc option medium. Leaving one portion of the reaction mix for measurement of background internalization and one portion for total binding measurement on ice, we incubated the rest of the reaction mix at 37° C. for 15 minutes, 30 minutes, and 1 h, 2, 4, and 8 hours. We washed the cells twice with ice-cold PBS and in a cold centrifuge. Except for the total binding portion, we resuspended all cells in 500 nM quenching anti-Alexa Fluor™-488 dye antibody (Invitrogen) diluted in ice-cold PBS. All tubes were incubated for 1 hour on ice. We washed the cells twice in ice-cold PBS and resuspended them in 4% paraformaldehyde; we analyzed the reaction samples in a flow cytometer (FACSCalibur™ flow cytometer, BD Biosciences, Franklin Lakes, N.J.). We calculated internalization as the fluorescence of quenched cells (intracellular compartments only) divided by that of unquenched cells (both cell surface and intracellular compartments; total binding) after normalization against the background fluorescence. The cells incubated with Alexa Fluor™-488 dye-labeled immunotoxins on ice were used as a control while estimating the antibody's quenching efficiency on each Alexa Fluor™-488 dye-labeled immunotoxin. Since internalization should not occur at 0° C., the fluorescence of these cells measured after quenching with anti-Alexa Fluor™-488 dye was considered to represent the unquenchable surface fluorescence (background). This amount was corrected when the percentage internalized immunotoxin was calculated.

Cell Culture.

We used the human malignant glioma-derived cell lines D54 MG and H336, which were established and maintained in our laboratory, as ganglioside-expressing cell lines. We used the human embryonic kidney cell line H293 as a negative control. We cultured all cell lines in Improved MEM Zinc Option (Richter's zinc option; Invitrogen) supplemented with 10% FBS (Invitrogen) and passed at confluence with 0.25% trypsin-EDTA (Invitrogen).

Disaggregation of Xenograft Tumor Samples.

Xenograft tissues from malignant gliomas (H2224 and BT56) obtained under sterile conditions from animals housed in the Duke Cancer Center Isolation Facility were prepared for cell culture in a laminar flow hood by using a sterile technique. Tumor material was finely cut with scissors and added to a trypsinizing flask containing approximately 10 mL of 100 μg Liberase (Roche, Indianapolis, Ind.). This mixture was stirred at 37° C. for 10 minutes, and cell-rich supernatant was obtained. We filtered the dissociated cells through a 100-μm cell strainer (BD Falcon, BD Biosciences), washed them with complete medium, and pelleted them at 1000 rpm for 5 minutes. We further treated the cell suspension with Ficoll-Hypaque to remove any red blood cells and then washed it once in complete medium. We cultured and passaged the cells until sufficient numbers were obtained and harvested them with 0.25% trypsin-EDTA.

Results:

Construction of the $V_H$CDR2 and $V_L$CDR1 Libraries.

We improved the affinity of DMAb14 (scFv) through random mutagenesis based on hot spots within either the $V_H$CDR2 region or the $V_L$CDR1 region, because these portions of the antibody might have significant contact with the antigens. The amino acid sequences of $V_H$CDR2 and $V_L$CDR1 are shown in Table 5. The libraries introduced randomizations in the hot spot motif residues S75, N76, G77, K86, S87, and K88 for $V_H$CDR2 and R25, A26, S27, S32, and Y33 for $V_L$CDR1 in separate experiment sets as described in "Materials and Methods." In the step of cloning, 3 $V_H$ libraries were mixed and yielded $6 \times 10^4$ clones, and 4 $V_L$ libraries yielded $5 \times 10^4$ clones. We sequenced 20 clones from the $V_H$ library and 14 from the $V_L$ library to verify that the construction of the library was appropriate. Sequencing showed that each clone had different amino acid combinations in the region targeted for mutations. The size of the libraries ensured that most of the DNA sequences were represented (data not shown).

TABLE 5

Nucleotide and amino acid sequence of heavy-chain CDR2 and light-chain CDR1 with hot spots of DMAb14 are shown*

| DMAb14 | GAG | ATT | AAT | CCT | AGC | AAC | GGT | GGT | GGT | AAC | TAT | AAT | GAG | AAG | TTC | AAG | AGC | AAG |
|---|---|---|---|---|---|---|---|---|---|---|---|---|---|---|---|---|---|---|
| $V_H$CDR2 | E | I | N | P | S | N | G | R | T | N | Y | N | E | K | F | K | S | K |

TABLE 5-continued

Nucleotide and amino acid sequence of heavy-chain CDR2 and light-chain CDR1 with hot spots of DMAb14 are shown*

| Position | 71 | 72 | 73 | 74 | 75 | 76 | 77 | 78 | 79 | 80 | 81 | 82 | 83 | 84 | 85 | 86 | 87 | 88 |
|---|---|---|---|---|---|---|---|---|---|---|---|---|---|---|---|---|---|---|
| DMAb14 | AGA | GC C | AGT | GAA | AGT | GTT | GAG | AGT | TAT | GGC | AAT | AAT | TTT | ATG | CAC | | | |
| | | | | | | | | | | | | | | | | | | |
| V$_L$CDR1 | R | A | S | E | S | V | E | S | Y | G | N | N | F | M | H | | | |
| Position | 25 | 26 | 27 | 28 | 29 | 30 | 31 | 32 | 33 | 34 | 35 | 36 | 37 | 38 | 39 | | | |

*Hot-spot positions are indicated with underline and boldface. Sequences shown on lines 1, 2, 4, and 5 of the Table are SEQ ID NOS: 46-49, respectively.

Selection of V$_H$CDR2 and V$_L$CDR1 Libraries and Analysis of Selected Clones.

We rescued recombinant phages from 500 individual phage clones from each library, and we randomly selected and tested these phages for reactivity against purified gangliosides by phage ELISA. We found that 10 clones from the V$_H$ library and 8 clones from the V$_L$ library showed high signals on ELISA. We repeatedly tested the selected clones with phage ELISA and sequenced them, and we finally found two clones from the V$_H$ library and three from the V$_L$ library that constantly exhibited strong signals during reaction with gangliosides and contained full-length scFv without stop codons (Table 6). V$_H$CDR2 mutant clones 86-MDS and 126-LPP retained the same residues as the parental V$_H$ at positions 86-88, but these two clones exhibited mutations at S75M, N76D, G77S and S75L, N76P, G77P, respectively. The V$_L$CDR1 mutant clone 23-RA showed mutations at S27R and S29A, whereas the mutant clones 104-PWR and 184-LYG showed PWR and LYG respectively at positions 25-27 in place of RAS in the parental clone (Table 6).

Binding Properties and Cytotoxicity of V$_H$CDR2 and V$_L$CDR1 Mutants.

We prepared V$_H$CDR2 and V$_L$CDR1 mutant immunotoxin clones and measured their cytotoxic activities and binding affinities using purified recombinant immunotoxin proteins on D54 glioblastoma cells. The V$_H$CDR2 mutants did not show improved binding affinity. Mutant clone 86-MDS, with mutations at positions V$_H$ 75-77, had an affinity of K$_d$=0.9 µM, and the affinity of clone 126-LPP ($K_d$=280 µM) was comparable to that of the parental clone ($K_d$=0.45 µM) (Table 6). Of the three V$_L$CDR1 mutants, clone 184-LYG showed better binding affinity ($K_d$=0.2 µM) than both the parental and the V$_H$CDR2 mutant clones. The other two V$_L$CDR1 mutant clones, 23-RA ($K_d$=0.8 µM) and 104-PWR ($K_d$=4.7 µM), did not display improved affinity as compared with the parental and V$_H$CDR2 mutant clones (Table 6). None of V$_H$CDR2 and V$_L$CDR1 mutant immunotoxins showed any significant cytotoxic activity in the protein-synthesis inhibition assay (data not shown).

Construction of Combination V$_H$CDR2 and V$_L$CDR1 Mutant.

Our goal was to obtain a scFv with increased affinity for gangliosides, which when converted to an immunotoxin would improve cytotoxic activity toward cells expressing gangliosides. Neither V$_H$CDR2 nor V$_L$CDR1 affinity-matured mutants showed improved binding affinity when compared with that of the parental clone or any significant cytotoxic activity. We therefore combined the V$_H$ and V$_L$ mutants to form a scFv with mutations in both V$_H$CDR2 and

TABLE 6

Positive clones were selected from the V$_H$CDR2 and V$_L$CDR1 libraries*

| | | | | | | | | | | | | | | | | | | | IC$_{50}$ (ng/ml) | K$_d$ (µM) |
|---|---|---|---|---|---|---|---|---|---|---|---|---|---|---|---|---|---|---|---|---|
| Position: DMAb14-V$_H$CDR2 | 71 | 72 | 73 | 74 | 75 | 76 | 77 | 78 | 79 | 80 | 81 | 82 | 83 | 84 | 85 | 86 | 87 | 88 | | |
| Original Amino Acid DMAb14-V$_H$CDR2 Mutant# | E | I | N | P | S | N | G | R | T | N | Y | N | E | K | F | K | S | K | N/A | N/A |
| No. 86 | E | I | N | P | M | D | S | R | T | N | Y | N | E | K | F | K | S | K | N/A | 0.9 |
| No. 126 | E | I | N | P | L | P | P | R | T | N | Y | N | E | K | F | K | S | K | N/A | 280 |
| Position: DMAb14-V$_L$CDR1# | 25 | 26 | 27 | 28 | 29 | 30 | 31 | 32 | 33 | 34 | 35 | 36 | 37 | 38 | 39 | | | | | |
| Original Amino Acid DMAb14-V$_L$CDR1Mutant | R | A | S | E | S | V | E | S | Y | G | N | N | F | M | H | | | | N/A | N/A |
| No. 23 | R | A | R | E | A | V | E | S | Y | G | N | N | F | M | H | | | | N/A | 0.8 |
| No. 104 | P | W | R | E | S | V | E | S | Y | G | N | N | F | M | H | | | | N/A | 4.7 |
| No. 184 | L | Y | G | E | S | V | E | S | Y | G | N | N | F | M | H | | | | N/A | 0.2 |

*Hot-spot positions are indicated with underline and boldface.
When VHCDR2 had mutations, VLCDR1 kept parental residues. When VLCDR1 had mutations, VHCDR2 kept parental residues. Lines of sequence 1 2, 3, 4, 5, 6, and 7 of the table show SEQ ID NO: 50-56, respectively V$_L$CDR1. We constructed six recombinant clones as described in "Materials and Methods" and prepared the immunotoxins as the following scFvs: DMAb14-8623-PEKDEL, DMAb14-86104-PEKDEL, DMAb14-86184-PEKDEL, DMAb14-12623-PEKDEL, DMAb14-126104-PEKDEL, and DMAb14-126184-PEKDEL (Table 7). We purified each immunotoxin to over 90% homogeneity and eluted it as a monomer by using TSK gel filtration chromatography (Sigma-Aldrich Co., St. Louis, Mo.) (results not shown). We used the purified immunotoxins in cytotoxicity assays and binding property measurement by flow cytometry.

TABLE 7

The combination mutant clones have mutations in both V$_H$CDR2 and V$_L$CDR1*

| | V$_H$CDR2 | V$_L$CDR1 |
|---|---|---|
| DMAb14-8623 | E I N P M D S R T N Y N E K F K S K | R A R E A V E S Y G N N F M H |
| DMAb14-86104 | E I N P M D S R T N Y N E K F K S K | P W R E S V E S Y G N N F M H |
| DMAb14-86184 | E I N P M D S R T N Y N E K F K S K | L Y G E S V E S Y G N N F M H |
| DMAb14-12623 | E I N P L P P R T N Y N E K F K S K | R A R E A V E S Y G N N F M H |
| DMAb14-126104 | E I N P L P P R T N Y N E K F K S K | P W R E S V E S Y G N N F M H |
| DMAb14-126184 | E I N P L P P R T N Y N E K F K S K | L Y G E S V E S Y G N N F M H |

*Hot-spot positions are indicated with underline and boldface. Lines of VHCDR2 sequence are SEQ ID NO: 57-62, respectively, and lines of VLCDR1 are SEQ ID NO: 63-68, respectively.

Binding Affinity of Combined Mutants Toward Cell Lines.

To determine whether the increased activity of the combined mutant immunotoxins was attributable to increased binding affinities, we measured affinity by using established flow cytometry as described in "Materials and Methods." The binding affinities of the six combined affinity-matured DMAb14 immunotoxins toward D54 MG cells are summarized in Table 8; these immunotoxins were found to be capable of binding to ganglioside-expressing cells on flow cytometric analysis. Two of the combined mutant immunotoxins, DMAb14-86184 and DMAb14-12623, showed increased binding affinity toward D54 MG cells, about 7 to 35 times higher than that of the V$_H$CDR2 or V$_L$CDR1 positive clones alone (Table 6) and about 10 to 15 times higher than that of the parental DMAb14 immunotoxin (profile data not shown). The mutant with the highest affinity was DMAb14-86184-MDSLYG, with a K$_d$ of 26.5 nM. DMAb14-86-MDS showed a K$_d$ of 900 nM, DMAb14-184-LYG a K$_d$ of 200 nM, and parental DMAb14 a K$_d$ of 450 nM. The mutant DMAb14-12623 showed a K$_d$ of 28.8 nM and had a similar pattern to that of DMAb14-86184-MD-SLYG. The rest of the affinity-matured mutants did not show significantly improved binding affinities.

TABLE 8

Binding affinities and cytotoxic activities of combination mutant immunotoxins on the D54 MG cell line differ*

| | Kd (nM) | IC$_{50}$ (ng/mL) |
|---|---|---|
| DMAb14-Parental | 450 | N/A |
| DMAb14-8623 | 549.4 | N/A |
| DMAb14-86104 | 352.5 | N/A |
| DMAb14-86184 | 26.5 | 80 |
| DMAb14-12623 | 28.8 | N/A |
| DMAb14-126104 | 1420 | N/A |
| DMAb14-126184 | 127.1 | N/A |

*Boldface denotes affinity-matured mutants with significantly improved binding affinity.

Cytotoxic Activity of Combined Mutant Immunotoxins on Cell Lines.

Figure 8B:
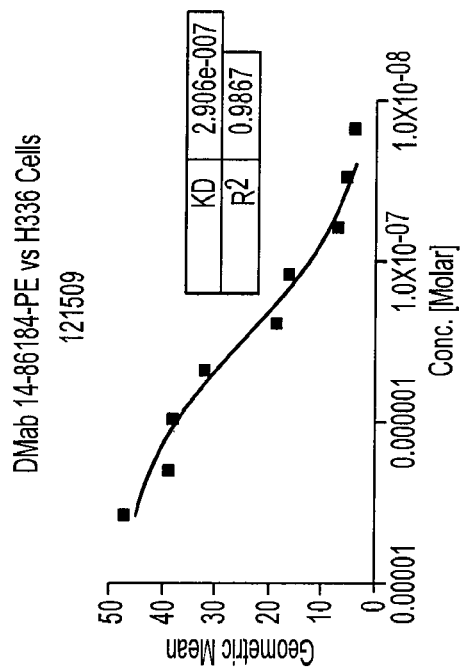
FIG. 8A-8B. DMab14-86184-scFv-PEKDEL protein binding affinity was measured on H336 cells by flow cytometry.
Figure 8A:
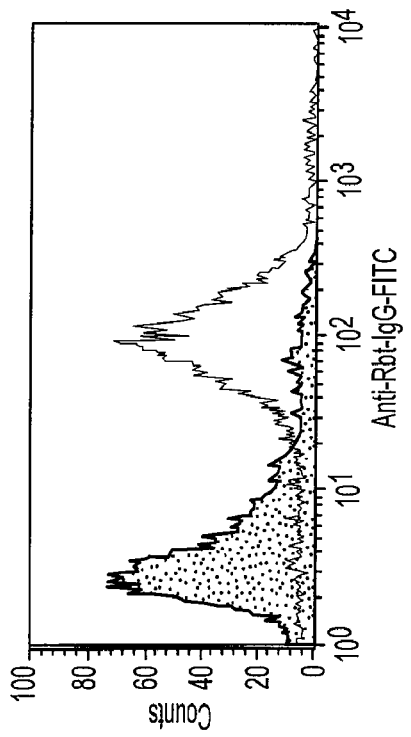
Figure 9A:
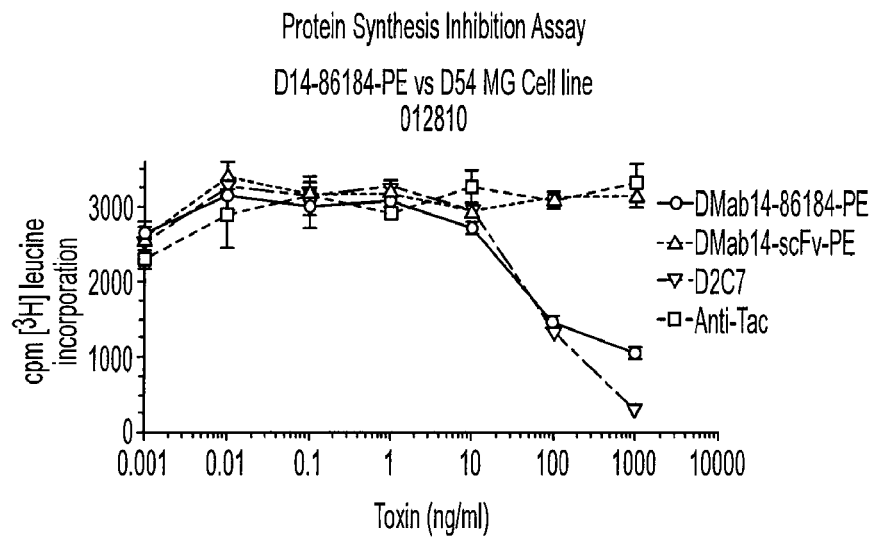
FIG. 9A-9B. Cytotoxicity of DMab14-86184-scFv-PEKDEL protein on both protein synthesis inhibition assay ($IC_{50}$=80 ng/ml) and cell proliferation assay ($IC_{50}$<1000 ng/ml) against D54 MG cells.
Figure 9B:
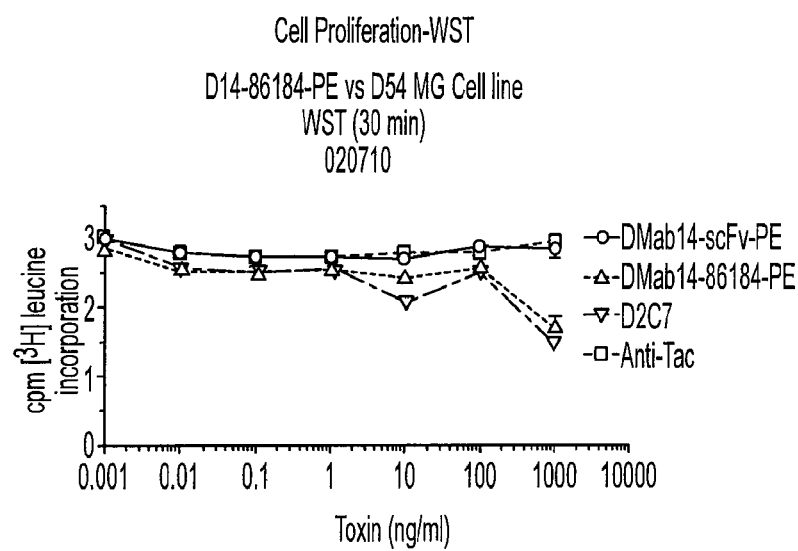
Figure 9C:
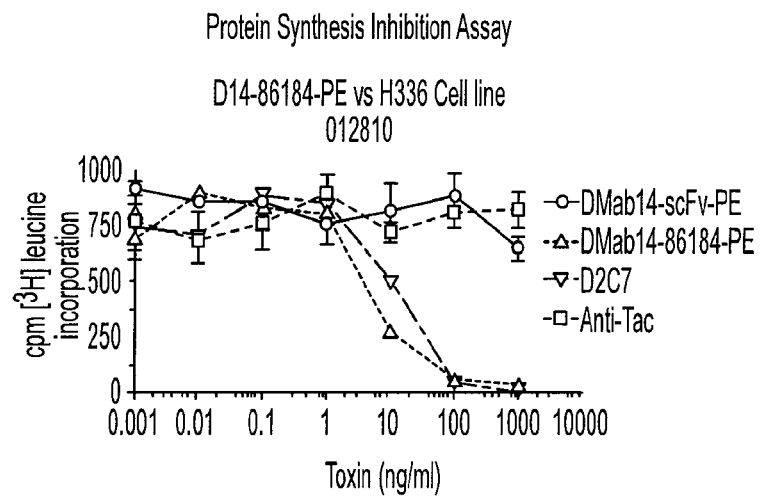
FIG. 9C-9D. Cytotoxicity of DMab14-86184-scFv-PEKDEL on both protein synthesis inhibition assay ($IC_{50}$=4 ng/ml) and cell proliferation assay ($IC_{50}$=15 ng/ml) against H336 cells.
Figure 9D:
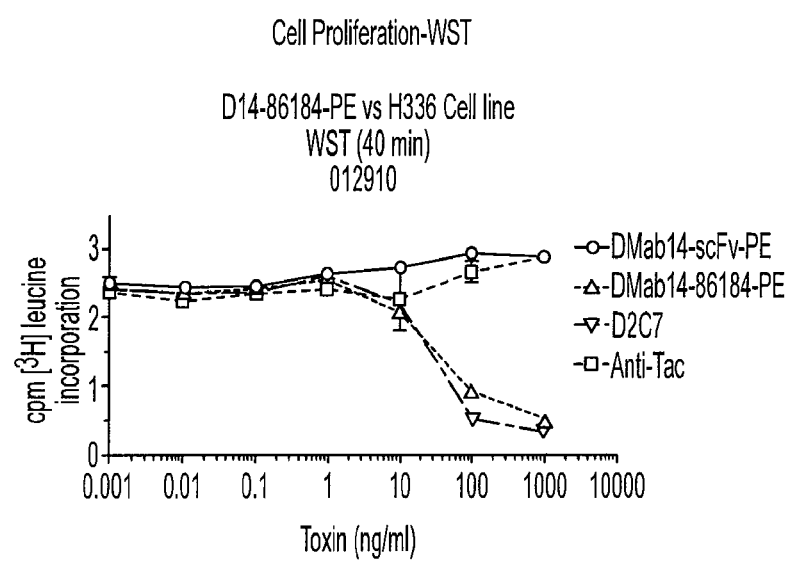

We next investigated the cytotoxic activity of the combined mutant immunotoxins on ganglioside-expressing D54 MG cells (FIG. 8). We purified each immunotoxin to over 90% homogeneity and eluted it as a monomer using TSK gel filtration chromatography (results not shown). As shown in FIG. 8, only one of the six combined affinity-matured mutant immunotoxins, namely, DMAb14-86184-PEKDEL, had cytotoxic activity on D54 MG cells, with an IC$_{50}$ of 80 ng/mL. The other combined mutant immunotoxins did not show significant cytotoxic activities on D54 MG cells (data not shown). Thus, we selected clone DMAb14-86184-PEKDEL, renaming it DMAb14-scFv-Mut-PEKDEL, for further studies.

DMAb14-scFv-Mut IT Epitope Mapping.

DMAb14-scFv ITs specifically bind to gangliosides 3'-isoLM1 and 3'6'-isoLD1, as shown in FIG. 9. Both DMAb14-scFv parental and DMAb14-scFv-Mut ITs showed significantly higher signals upon reaction with gangliosides 3'-isoLM1 and 3'6'-isoLD1 than those shown by the structural negative control D2C7-IT. We used different reaction systems for scFv-IT and positive IgMs; nonetheless, significantly higher signals were obtained for SL50 IgM (antibody for 3'-isoLM1) and DMAb22 μM (antibody for 3'6'-isoLD1) than for negative control MOPC IgM on 3'-isoLM1 and 3'6'-isoLD1, respectively, indicating that the gangliosides were properly coated.

Cytotoxic Activity of DMAb14-scFv-Mut Immunotoxin on Cell Lines and Xenografts.

We further tested the cytotoxic activity of DMAb14-scFv-Mut-PEKDEL on different cell lines and xenografts known to express cell-surface gangliosides. We evaluated cytotoxicity (IC$_{50}$) on the basis of both the protein synthesis inhibition assay ([$^3$H] leucine incorporation) and the cell death assay (WST-8) (FIG. 10). The parental DMAb14-scFv-PEKDEL did not display any cytotoxic activity on any ganglioside-expressing cells. In contrast, the affinity-matured DMAb14-Mut-IT exhibited an IC$_{50}$ of 2 ng/mL (29.9 pM) toward H336 cells, a malignant glioblastoma cell line (FIG. 10A, 10B), and an IC$_{50}$ of 0.5 ng/mL (7.5 pM) toward xenograft cells 2224, also derived from a malignant glioblastoma (tumor block from Duke Hospital) (FIG. 10C, 10D). DMAb14-Mut-IT showed the highest cytotoxic activity toward xenograft cells 2224, 4-fold greater than its activity on H336 cells. The mutant immunotoxin was not cytotoxic to the ganglioside-negative cell line D293 (a human embryonic kidney 293 cell line established by Duke University; data not shown), indicating that the cytotoxic effect of this immunotoxin is selective to antigen-positive cells.

Binding of DMAb14-scFv-Mut Immunotoxin to H336 Cells.

In order to accurately determine the dissociation constant value, we performed a cell-binding assay using isotope-direct-labeled immunotoxin reacting with ganglioside-expressing H336 cells. DMAb14-Mut immunotoxin was labeled with iodine 125, and its binding to live H336 cells at 4° C. was assayed as described in "Materials and Methods." The data were plotted for Scatchard analysis (FIG. 11); the slope of the plot thus obtained was 0.38 nM$^{-1}$, giving a $K_d$ of 2.6 nM, and its regression coefficient was 0.982. This $K_d$ value is 10 times lower than that measured by flow cytometry of the same H336 cells.

Internalization of DMAb14-scFv-Mut Immunotoxin in H336 Cells.

We quenched surface fluorescence by using anti-Alexa-488 antibody in order to determine the internalized fraction. Internalization was measured as a percentage of the total amount bound to ganglioside binders by comparing the Alexa-488 fluorescence of the quenched cells (intracellular compartment) to that of the unquenched cells (both intracellular and cell-surface compartments) by using flow cytometric analysis. Unquenchable surface fluorescence (background) was estimated in parallel tubes on ice (no internalization at 0° C.). The amount of unquenchable fluorescence of Alexa-488-labeled DMAb14-scFv-Mut and DMAb14-scFv parental immunotoxins was about 24% and 8.5%, respectively, when incubated with H336 cells and 13% and 1.2%, respectively, when incubated with xenograft 2224 cells (FIG. 12). We corrected each individual experiment for this "background fraction" before calculating the internalization percentage.

As the duration of incubation at 37° C. increased, the internalization percentage of DMAb14-scFv-Mut-IT in H336 cells increased gradually at first (0.82% at 15 minutes, 14% at 30 minutes, 16% at 1 hour, 30% at 2 hours) and then dramatically increased to 98% at 4 hours, eventually reaching 100% at 8 hours. In contrast, the internalization percentage of DMAb14-scFv parental immunotoxin fluctuated between 6% and 12% and was not significant throughout the incubation period (FIG. 12A). DMAb14-scFv-Mut-IT internalization into xenograft 2224 cells began increasing after 30 minutes and reached 43% at 1 hour, 80% at 2 hours, 94% at 4 hours, and 100% at 8 hours. The DMAb14-scFv parental immunotoxin did not show significant internalization in the xenograft 2224 cells (FIG. 12B).

Discussion:

Our goal was to develop an anti-ganglioside scFv immunotoxin with high cytotoxic activity and tumor specificity. The approach used to increase the affinity of the parental MAb, DMAb14-scFv, was to mutagenize hot spot residues in $V_H$CDR2 and $V_L$CDR1. Hot spots are regions of DNA that are frequently mutated during the in vivo affinity maturation of antibodies. In contrast with other strategies for increasing antibody affinity, our approach of targeting hot spots allowed us to make a small library (4×10$^4$ clones) that covered all possible mutations. We were able to identify several different mutations that conferred increased affinity, and when the mutations in $V_H$CDR2 and $V_L$CDR1 were combined in a single clone, the antibody's affinity was even higher.

While the analysis of mutant clones selected by phage ELISA screening revealed the presence of a variety of different sequences, there was a pattern to the amino acid substitutions (Table 6). In the mutant clones, three amino acids of $V_H$CDR2 (75-77) and three of $V_L$CDR1 (25-27) were consistently different from the parental sequence, which indicates that these residues are required for interacting with the antigens. When the three mutations in $V_H$CDR2 and the three mutations in $V_L$CDR1 were combined in one scFv construct (DMAb14-scFv-86184-PEKDEL, hereafter referred to as DMAb14-scFv-Mut-IT), the clone showed improved binding affinity (Tables 7 and 8) and dramatic cytotoxic activity (FIG. 8 and FIG. 10). It is possible that the $V_H$ and $V_L$ loop may require all these residues together for proper conformational flexibility, not only to achieve increased affinity but also to enable better structural conformation for internalization as compared to the parental clone and other mutant clones.

We confirmed that both the parental DMAb14-scFv-IT and mutant DMAb14-scFv-Mut-IT react with purified 3'-isoLM1 and 3',6'-isoLD1, whereas D2C7-scFv-IT, which is an antibody to EGFRvIII and wild-type EGFR, does not (FIG. 9). In addition, both DMAb14-scFv-Mut-IT and D2C7-scFv-IT show significant cytotoxicity against GBM tumor cells. Since these two immunotoxins target different tumor antigens, D2C7-scFv-IT is an excellent positive control for cytotoxicity in our study.

The IC$_{50}$ values of the DMAb14-scFv-Mut-IT varied among the different cell lines and xenografts tested (FIG. 10), probably due to different numbers of gangliosides on the cell surfaces. It is also possible that 3'-isoLM1 and 3',6'-isoLD1 are present at different proportions on different cell types. Xenograft H2224 cells have been screened by an anti-ganglioside monoclonal antibody specific for 3'-isoLM1 (10) and 3',6'-isoLD1 (18), which revealed that 88% of 112224 cells were positive for 3'-isoLM1 and 2% for 3',6'-isoLD1. Therefore, 3'-isoLM1 is the main ganglioside expressed on H2224 tumor cells. We also determined that the xenograft H2224 cells have a higher ratio of 3'-isoLM1 to 3',6'-isoLD1 than H336 and D54 MG cells (data not shown). Since DMAb14-scFv-Mut-IT has a more potent effect on xenograft H2224 cells (IC$_{50}$ of 0.5 ng/mL) than on H336 cells (IC$_{50}$ of 2 ng/mL), DMAb14-scFv-Mut-IT may have a greater affinity for 3'-isoLM1 and greater benefit for patients with 3'-isoLM1-dominant brain tumors.

The DMAb14-scFv parental and mutant immunotoxins differ only at the targeted amino acid residues. Both show specificity and binding affinity to the ganglioside-positive cells; however, only the mutant IT displays cytotoxic activity. Therefore we sought to determine whether the immunotoxins were differentially internalized by the cells. Recombinant immunotoxins are chimeric proteins used for cancer therapy, consisting of a targeting moiety linked to the catalytic domains of a natural toxin (19). We utilized *Pseudomonas* exotoxin A (PE38), which is a potent bacterial toxin composed of three domains (20) that is able to enter tumor cells and inhibit protein synthesis, eventually killing the cell. We found that DMAb14-scFv-Mut-IT is internalized significantly faster than the parental IT, with xenograft H2224 cells and H336 cells internalizing 94% and 98% of DMAb14-scFv-Mut-IT, respectively, within 4 hours and internalizing no significant amount of the parental IT within the same time period (FIG. 12). Xenograft H2224 cells internalized the mutant IT faster than H336 cells, which may explain why DMAb14-scFv-Mut-IT is more potent in H2224 cells.

In summary, we developed an anti-ganglioside scFv immunotoxin with high cytotoxic activity and tumor specificity. We achieved this goal using intrinsic mutational hot spots as targets for antibody affinity maturation in vitro. The parental clone DMAb14-scFv-IT had the proper affinity but did not have any cytotoxic activity, whereas the selected mutant, DMAb14-scFv-Mut-IT, showed a much higher affinity and increased cytotoxic activity to ganglioside-positive cell lines and tumor xenograft cells. DMAb14-scFv-Mut-IT exhibited strong cytotoxic effects on the human glioblastoma xenograft cell line H2224 (IC$_{50}$=0.5 ng/mL) and no cytotoxic effects on the ganglioside-negative cell line D293, demonstrating the selectivity of the immunotoxin. Moreover, the increased cytotoxic activity of the mutant immunotoxin could provide a clinical benefit with a low dose, which would decrease nonspecific toxicities in patients. This study is, to the best of our knowledge, the first time a scFv recombinant immunotoxin targeting 3'-isoLM1 and 3',6'-isoLD1 gangliosides has been shown to have significant specificity, high binding affinity, and dramatic cytotoxic activity in tumor cells. Our findings strongly suggest that this immunotoxin has great potential for clinical diagnosis and therapy for patients with brain tumors and warrants further preclinical studies.

REFERENCES FOR EXAMPLE 6 ONLY

The disclosure of each reference cited is expressly incorporated herein.
1. Wong E T, K R Hess, M J Gleason, et al. Outcomes and prognostic factors in recurrent glioma patients enrolled onto phase II clinical trials. J Clin Oncol 1999; 17:2572-8.
2. Waldmann T A. Monoclonal antibodies in diagnosis and therapy. Science 1991; 252:1657-62.
3. Wu A M, P D Senter. Arming antibodies: prospects and challenges for immunoconjugates Nat Biotechnol 2005; 23:1137-46.
4. Vukelic Z, S Kalanj-Bognar, M Froesch, et al. Human gliosarcoma-associated ganglioside composition is complex and distinctive as evidenced by high-performance mass spectrometric determination and structural characterization. Glycobiology 2007; 17:504-15.
5. Liu Y, S Yan, A Wondimu, et al. Ganglioside synthase knockout in oncogene-transformed fibroblasts depletes gangliosides and impairs tumor growth Oncogene 2010; 29:3297-306.
6. Wikstrand C J, P Fredman, L Svennerholm, P A Humphrey, S H Bigner, D D Bigner. Monoclonal antibodies to malignant human gliomas Mol Chem Neuropathol 1992; 17:137-46.
7. Fredman P. Gangliosides associated with primary brain tumors and their expression in cell lines established from these tumors. Prog Brain Res 1994; 101:225-40.
8. Fredman P, K Hedberg, T Brezicka. Gangliosides as therapeutic targets for cancer. BioDrugs 2003; 17:155-67.
9. Gottfries J, J E Mansson, P Fredman, et al. Ganglioside mapping of a human medulloblastoma xenograft. Acta Neuropathol 1989; 77:283-8.
10. Wikstrand C J, X M He, G N Fuller, et al. Occurrence of lacto series gangliosides 3'-isoLM1 and 3',6'-isoLD1 in human gliomas in vitro and in vivo. J Neuropathol Exp Neurol 1991; 50:756-69.
11. Archer G E, J H Sampson, I A Lorimer, et al. Regional treatment of epidermal growth factor receptor vIII-expressing neoplastic meningitis with a single-chain immunotoxin, MR-1. Clin Cancer Res 1999; 5:2646-52.
12. Kuan C T, C J Reist, C F Foulon, et al. 125I-labeled anti-epidermal growth factor receptor-vIII single-chain Fv exhibits specific and high-level targeting of glioma xenografts Clin Cancer Res 1999; 5:1539-49.
13. Yokota T, D E Milenic, M Whitlow, J Schlom. Rapid tumor penetration of a single-chain Fv and comparison with other immunoglobulin forms Cancer Res 1992; 52:3402-8.
14. Pastan I H, G E Archer, R E McLendon, et al. Intrathecal administration of single-chain immunotoxin, LMB-7 [B3 (Fv)-PE38], produces cures of carcinomatous meningitis in a rat model. Proc Natl Acad Sci USA 1995; 92:2765-9.
15. Buchner J, I Pastan, U Brinkmann. A method for increasing the yield of properly folded recombinant fusion proteins: single-chain immunotoxins from renaturation of bacterial inclusion bodies. Anal Biochem 1992; 205:263-70.
16. Ho M, R J Kreitman, M Onda, I Pastan. In vitro antibody evolution targeting germline hot spots to increase activity of an anti-CD22 immunotoxin. J Biol Chem 2005; 280: 607-17.
17. Kadan M J, S Sturm, W F Anderson, M A Eglitis. Detection of receptor-specific murine leukemia virus binding to cells by immunofluorescence analysis J Virol 1992; 66:2281-7.
18. Wikstrand C J, P Fredman, L Svennerholm, D D Bigner. Detection of glioma-associated gangliosides GM2, GD2, GD3,3'-isoLM1 3',6'-isoLD1 in central nervous system tumors in vitro and in vivo using epitope-defined monoclonal antibodies. Prog Brain Res 1994; 101:213-23.
19. Pastan I, D FitzGerald. Recombinant toxins for cancer treatment Science 1991; 254:1173-7.
20. Allured V S, RJ Collier, S F Carroll, D B McKay. Structure of exotoxin A of *Pseudomonas aeruginosa* at 3.0-Angstrom resolution. Proc Natl Acad Sci USA 1986; 83:1320-4.

REFERENCES FOR ALL BUT EXAMPLE 6

The disclosure of each reference cited is expressly incorporated herein.
[1] Hakomori, S. I. (2008) Structure and function of glycosphingolipids and sphingolipids: recollections and future trends. Biochim. Biophys. Acta 1780, 325-346.
[2] Bowes, T., Wagner, E. R., Boffey, J., Nicholl, D., Cochrane, L., Benboubetra, M., Conner, J., Furukawa, K., Furukawa, K. and Willison, H. J. (2002) Tolerance to self gangliosides is the major factor restricting the antibody response to lipopolysaccharide core oligosaccharides in *Campylobacter jejuni* strains associated with Guillain-Barre syndrome. Infect. Immun. 70, 5008-5018.
[3] Akeboshi, H., Chiba, Y., Kasahara, Y., Takashiba, M., Takaoka, Y., Ohsawa, M., Tajima, Y., Kawashima, I., Tsuji, D., Itoh, K., Sakuraba, H. and Jigami, Y. (2007) Production of recombinant beta-hexosaminidase A, a potential enzyme for replacement therapy for Tay-Sachs and Sandhoff diseases, in the methylotrophic yeast *Ogataea minuta*. Appl. Environ. Microbiol. 73, 4805-4812.
[4] Kawashima, N., Tsuji, D., Okuda, T., Itoh, K. and Nakayama, K. I. (in press) Mechanism of abnormal growth in astrocytes derived from a mouse model of GM2 gangliosidosis. J. Neurochem.
[5] Kawashima, I., Nakamura, O. and Tai, T. (1992) Antibody responses to ganglio-series gangliosides in different strains of inbred mice. Mol. Immunol. 29, 625-632.
[6] Lunn, M. P., Johnson, L. A., Fromholt, S. E., Itonori, S., Huang, J., Vyas, A. A., Hildreth, J. E., Griffin, J. W., Schnaar, R. L. and Sheikh, K. A. (2000) High-affinity anti-ganglioside IgG antibodies raised in complex ganglioside knockout mice: reexamination of GD1a immunolocalization. J. Neurochem. 75, 404-412.
[7] Ozawa, H., Kotani, M., Kawashima, I. and Tai, T. (1992) Generation of one set of monoclonal antibodies specific for b-pathway ganglio-series gangliosides. Biochim. Biophys. Acta 1123, 184-190.
[8] Liu, Y., Wada, R., Kawai, H., Sango, K., Deng, C., Tai, T., McDonald, M. P., Araujo, K., Crawley, J. N., Bierfreund, U., Sandhoff, K., Suzuki, K. and Proia, R. L. (1999)

A genetic model of substrate deprivation therapy for a glycosphingolipid storage disorder. J. Clin. Invest. 103, 497-505.

[9] Takamiya, K., Yamamoto, A., Furukawa, K., Yamashiro, S., Shin, M., Okada, M., Fukumoto, S., Haraguchi, M., Takeda, N., Fujimura, K., Sakae, M., Kishikawa, M., Shiku, H., Furukawa, K. and Aizawa, S. (1996) Mice with disrupted GM2/GD2 synthase gene lack complex gangliosides but exhibit only subtle defects in their nervous system. Proc. Natl. Acad. Sci. USA 93, 10662-10667.

[10] Okada, M., Itoh Mi, M., Haraguchi, M., Okajima, T., Inoue, M., Oishi, H., Matsuda, Y., Iwamoto, T., Kawano, T., Fukumoto, S., Miyazaki, H., Furukawa, K., Aizawa, S, and Furukawa, K. (2002) b-series Ganglioside deficiency exhibits no definite changes in the neurogenesis and the sensitivity to Fas-mediated apoptosis but impairs regeneration of the lesioned hypoglossal nerve. J. Biol. Chem. 277, 1633-1636.

[11] Okuda, T., Tokuda, N., Numata, S., Ito, M., Ohta, M., Kawamura, K., Wiels, J., Urano, T., Tajima, O., Furukawa, K. and Furukawa, K. (2006) Targeted disruption of Gb3/CD77 synthase gene resulted in the complete deletion of globo-series glycosphingolipids and loss of sensitivity to verotoxins. J. Biol. Chem. 281, 10230-10235.

[12] Kondo, Y., Tokuda, N., Fan, X., Yamashita, T., Honke, K., Takematsu, H., Togayachi, A., Ohta, M., Kotzusumi, Y., Narimatsu, H., Tajima, O., Furukawa, K. and Furukawa, K. (2009) Glycosphingolipids are not pivotal receptors for Subtilase cytotoxin in vivo: sensitivity analysis with glycosylation-defective mutant mice. Biochem. Biophys. Res. Commun. 378, 179-181.

[13] Boffey, J., Nicholl, D., Wagner, E. R., Townson, K., Goodyear, C., Furukawa, K., Furukawa, K., Conner, J. and Willison, H. J. (2004) Innate murine B cells produce anti-disialosyl antibodies reactive with Campylobacter jejuni LPS and gangliosides that are polyreactive and encoded by a restricted set of unmutated V genes. J. Neuroimmunol. 152, 98-111.

[14] Boffey, J., Odaka, M., Nicoll, D., Wagner, E. R., Townson, K., Bowes, T., Conner, J., Furukawa, K. and Willison, H. J. (2005) Characterisation of the immunoglobulin variable region gene usage encoding the murine anti-ganglioside antibody repertoire. J. Neuroimmunol. 165, 92-103.

[15] Henion, T. R., Zhou, D., Wolfer, D. P., Jungalwala, F. B. and Hennet, T. (2001) Cloning of a mouse beta 1,3 N-acetylglucosaminyltransferase GlcNAc(beta 1,3)Gal (beta 1,4)Glc-ceramide synthase gene encoding the key regulator of lacto-series glycolipid biosynthesis. J. Biol. Chem. 276, 30261-30269.

[16] Wikstrand, C. J., He, X. M., Fuller, G. N., Bigner, S. H., Fredman, P., Svennerholm, L. and Bigner, D. D. (1991) Occurrence of lacto series gangliosides 3'-isoLM1 and 3',6'-isoLD1 in human gliomas in vitro and in vivo. J. Neuropathol. Exp. Neurol. 50, 756-769.

[17] Wikstrand, C. J., Longee, D. C., McLendon, R. E., Fuller, G. N., Friedman, H. S., Fredman, P., Svennerholm, L. and Bigner, D. D. (1993) Lactotetraose series ganglioside 3',6'-isoLD1 in tumors of central nervous and other systems in vitro and in vivo. Cancer Res. 53, 120-126.

[18] Wikstrand, C. J., Fredman, P., Svennerholm, L. and Bigner, D. D. (1994) Detection of glioma-associated gangliosides GM2, GD2, GD3,3'-isoLM1 3',6'-isoLD1 in central nervous system tumors in vitro and in vivo using epitope-defined monoclonal antibodies. Prog. Brain Res. 101, 213-223.

[19] Mansson, J. E., Fredman, P., Bigner, D. D., Molin, K., Rosengren, B., Friedman, H. S. and Svennerholm, L. (1986) Characterization of new gangliosides of the lactotetraose series in murine xenografts of a human glioma cell line. FEBS Lett. 201, 109-113.

[20] Kato, Y., Jin, G., Kuan, C. T., McLendon, R. E., Yan, H. and Bigner, D. D. (in press) A monoclonal antibody IMab-1 specifically recognizes IDH1$^{R132H}$, the most common glioma-derived mutation. Biochem. Biophys. Res. Commun.

The invention claimed is:

1. An isolated antibody construct which comprises the amino acid sequence shown in SEQ ID NO: 6, wherein the antibody construct binds to both 3'-isoLM1 and 3',6'-iso-LD1 gangliosides.

2. The isolated antibody construct of claim 1 which is attached to a cytotoxic moiety.

3. The isolated antibody construct of claim 2 wherein the cytotoxic moiety is selected from the group consisting of biological toxins and radiologic toxic moieties.

4. The isolated antibody construct of claim 3 wherein the cytotoxic moiety is *Pseudomonas* exotoxin A.

5. The isolated antibody construct of claim 3 wherein the cytotoxic moiety is the truncated form of *Pseudomonas* exotoxin A PE38.

* * * * *